United States Patent
Walia

(10) Patent No.: US 11,628,226 B2
(45) Date of Patent: *Apr. 18, 2023

(54) METHODS AND GENE THERAPY CONSTRUCTS FOR TREATING GM2 GANGLIOSIDOSES

(71) Applicants: Queen's University at Kingston, Kingston (CA); Kingston Health Sciences Centre, Kingston (CA)

(72) Inventor: Jagdeep Singh Walia, Kingston (CA)

(73) Assignees: Queen's University at Kingston, Kingston (CA); Kingston Health Sciences Centre, Kingston (CA)

( * ) Notice: Subject to any disclaimer, the term of this patent is extended or adjusted under 35 U.S.C. 154(b) by 51 days.

This patent is subject to a terminal disclaimer.

(21) Appl. No.: 17/325,417

(22) Filed: May 20, 2021

(65) Prior Publication Data

US 2022/0072151 A1    Mar. 10, 2022

Related U.S. Application Data

(63) Continuation of application No. 15/617,465, filed on Jun. 8, 2017, now Pat. No. 11,045,557.

(60) Provisional application No. 62/348,003, filed on Jun. 9, 2016.

(51) Int. Cl.
| | |
|---|---|
| *A61K 48/00* | (2006.01) |
| *C12N 15/86* | (2006.01) |
| *C12N 9/24* | (2006.01) |
| *A61K 31/405* | (2006.01) |
| *A61K 31/505* | (2006.01) |
| *A61K 38/47* | (2006.01) |
| *A61K 31/27* | (2006.01) |

(52) U.S. Cl.
CPC .............. *A61K 48/00* (2013.01); *A61K 31/27* (2013.01); *A61K 31/405* (2013.01); *A61K 31/505* (2013.01); *A61K 38/47* (2013.01); *C12N 9/2402* (2013.01); *C12N 15/86* (2013.01); *C12Y 302/01052* (2013.01); *C12N 2750/14143* (2013.01)

(58) Field of Classification Search
CPC .... A61K 48/00; C12N 15/86; C12N 2840/20; C12N 2800/10
See application file for complete search history.

(56) References Cited

U.S. PATENT DOCUMENTS

| | | |
|---|---|---|
| 11,045,557 B2 | 6/2021 | Walia |
| 2004/0192630 A1 | 9/2004 | Kyrkanides |
| 2013/0211380 A1 | 8/2013 | Cabrera Aquino et al. |

OTHER PUBLICATIONS

Maegawa. G.H.B., et al. "Pyrimethamine as a Potential Pharmacological Chaperone for Late-Onset Forms of GM2 Gangliosidosis" The Journal of Biological Chemistry 232, No. 12 (Mar. 23, 2007): 9150-61.
Martino, S., et al. "Beta-N-Acetylhexosaminidases A and S Have Similar Sub-Cellular Distributions in HL-60 Cells" Biochimica Et Biophysica Acta 1243, No. 3 (Apr. 13, 1995): 489-95.
Sandhoff, K., et al. "Gangliosides and Gangliosidoses: Principles of Molecular and Metabolic Pathogenesis" The Journal of Neuroscience: The Official Journal of the Society for Neuroscience 33, No. 25 (Jun. 19. 2013): 10195-208.
Tropak, M.B., et al. "Pharmacological enhancement of beta-hexosaminidase activity in fibroblasts from adult Tay-Sachs and Sandhoff Patients" Journal of Biological Chemistry 279(14) (2004): 13478-87.
Tropak, M.B., et al. "A Sensitive Fluorescence-based Assay for Monitoring GM2 Ganglioside Hydrolysis in Live Patient Cells and their Lysates" Glycobiology, 20(3) (2010): 356-365.
Wherrett, J.R., et al. "Detection and resolution of gangliosides in lipid extracts by thin-layer chromatography" Biochemical Journal, 86(2) (1963): 378-382.
Wu, Z., et al. "Effect of genome size on AAV vector packaging" Molecular Therapy 18(1)(2010): 80-86.
Third Party Submission under 37 CFR 1.290 for U.S. Appl. No. 15/617,465, filed Oct. 17, 2019.
Jeyakumar, M. et al., "NSAIDs Increase Survival in the Sandhoff Disease Mouse—Synergy with N-butyldeoxynojirimycin", Annals of Neurology, vol. 56, No. 5, pp. 642-649, (2004).
LeBec, C., et al., "Gene Therapy Progress and Prospects—Vectorology design and production of expression cassettes in AAV vectors", Gene Therapy, pp. 805-813, (2006).
Bera, L.A. "Adeno-associated virus gene therapy for Tay-Sachs disease", Master's thesis, University of Minnesota, Minneapolis, Minnesota, 2008.
Bourdenx, M., et al. "Systemic Gene Delivery to the Central Nervous System Using Adeno-Associated Virus" Frontiers in Molecular Neuroscience 7 (Jun. 2, 2014).
Faraco, G., et al. "Histone Deacetylase (HDAC) Inhibitors Reduce the Glial Inflammatory Response in Vitro and in Vivo" Neurobiology of Disease 36, No. 2 (Nov. 2009): 269-79.
Folch, J., et al. "Preparation of Lipid Extracts from Brain Tissue" Journal of Biological Chemistry, 191(2) (1951): 833-841.
Foust, K.D., et al. "Intravascular AAV9 Preferentially Targets Neonatal Neurons and Adult Astrocytes" Nature Biotechnology 27, No. 1 (Jan. 2009): 59-65.
Gray, S.J., et al. "Global CNS Gene Delivery and Evasion of Anti-AAV-Neutralizing Antibodies by Intrathecal AAV Administration in Non-Human Primates" Gene Therapy 20, No. 4 (Apr. 2013): 450-59.
Guidotti, J.E., et al. "Adenoviral gene therapy of the Tay-Sachs disease in hexosaminidase A-deficient knock-out mice" Human Molecular Genetics 8(5):831-8, 1999.

(Continued)

*Primary Examiner* — James D Schultz
*Assistant Examiner* — James Joseph Graber
(74) *Attorney, Agent, or Firm* — Stephen J. Scribner

(57) ABSTRACT

Disclosed are novel gene therapy constructs containing both HEXA and HEXB genes to treat GM2 gangliosidoses, including Sandhoff disease and Tay-Sach's disease. Also described are co-treatments using chaperone and anti-inflammatory agents to enhance the effects of gene therapy.

12 Claims, 11 Drawing Sheets

Specification includes a Sequence Listing.

(56) References Cited

OTHER PUBLICATIONS

Hitoshi, N., et al. "Efficient Selection for High-Expression Transfectants with a Novel Eukaryotic Vector" Gene 108, No. 2 (Dec. 15, 1991): 193-99.

Jun-ichi, M., et al. "Expression Vector System Based on the Chicken β-Actin Promoter Directs Efficient Production of Interleukin-5" Gene 79, No. 2 (Jul. 15, 1989): 269-77.

Kim, J.H., et al. "High Cleavage Efficiency of a 2A Peptide Derived from Porcine Teschovirus-1 in Human Cell Lines, Zebrafish and Mice" PLoS ONE 6, No. 4 (Apr. 29, 2011).

Clarke, J.T.R., et al., "An open-label Phase 1/11 clinical trial of pyrimethamine for the treatment of patients affected with chronic GM2 gangliosidosis—Tay-Sachs or Sandhoff variants", Molecular Genetics and Metabolism, vol. 102, pp. 1-18, (2011).

Arfi, A., et al., "Bicistronic lentiviral vector corrects Beta-hexosaminidase deficiency in transduced and cross-corrected human Sandhoff fibroblasts", Neurobiology of Disease, vol. 20, pp. 583-593, (2005).

Furler, S. et al., "Recombinant AAV vectors containing the foot and mouth disease virus 2A sequence confer efficient bicistronic gene expression in cultured cells and rat substantia nigra neurons", Gene Therapy, pp. 864-873, (2001).

Zhao, J-J, et al., "Increased Na+/Ca2+ Exchanger Activity Promotes Resistance to Excitotoxicity in Cortical Neurons of the Ground Squirrel (a Hibernator)" PLOS ONE I DOI.10.1371/journal.pone.0113594 pp. 1-20, (2014).

Kim, J. et al., "MGRASP enables mapping mammalian synaptic connectivity with light microscopy", Nature Methods, vol. 9, No. 1, pp. 96-104, (2011). GenBank Accession Code: JN898962.

Khoka et al., "Vectors for Expression Cloning in Xenopus", Direct Submission, 2006, Accession DQ649431, (2006).

De Felipe, P., et al., "E unum pluribus: multiple proteins from a self-processing polyprotein", TRENDS in Biotechnology, vol. 24, No. 2, pp. 68-75, (2002).

```
gctgcgcgct cgctcgctca ctgaggccgc ccgggcaaag cccgggcgtc gggcgacctt      60
tggtcgcccg gcctcagtga gcgagcgagc gcgcagagag ggagtggcca actccatcac     120
tagggttcc  ttgtagttaa tgattaaccc gccatgctac ttatctacgt agccatgctc     180
taggaagagt accattgacg tcaataatga cgtatgttcc catagtaacg ccaataggga     240
ctttccattg acgtcaatgg gtggagtatt tacgtaaac  tgcccacttg gcagtacatc     300
aagtgtatca tatgccaagt acgcccccta ttgacgtcaa tgacggtaaa tggcccgcct     360
ggcattatgc ccagtacatg accttatggg actttcctac ttggcagtac atctacgtat     420
tagtcatcgc tattaccatg gtcgaggtga gccccacgtt ctgcttcact ctccccatct     480
cccccccctc ccacccccaa attttgtatt tatttatttt ttaattattt tgtgcagcga     540
tgggggcggg ggggggggg  gggcgcgcgc caggcgggc  gggcggggc  gaggggcggg     600
gcggggcgag gcggagaggt gcggcggcag ccaatcagag cggcgcgctc cgaaagtttc     660
cttttatggc gaggcggcgg cggcggcggc cctataaaaa gcaagcgcg  cggcgggcgg     720
gagtcgctgc gcgctgcctt cgccccgtgc cccgctccgc cgccgctcg  cgccgcccgc     780
cccggctctg actgaccgcg ttactcccac aggtgagcgg gcggacggc  cctctcctc     840
cgggctgtaa ttagcgcttg gtttaatgac ggcttgtttc ttttctgtgg ctgcgtgaaa     900
gccttgaggg gctccgggag ggccctttgt gcggggggag cggctcgggg ctgtccgcgg     960
gggacggct  gccttcgggg gggacggggc agggcgggt  tcggcttctg gcgtgtgacc    1020
ggcggctcta gaatggagct gtgcggctg  gggctgcccc ggccgcccat gctgctggcg    1080
ctgctgttgg cgacactgct ggcggcgatg ttggcgctgc tgactcaggt ggcgctggtg    1140
gtgcaggtgg cggaggcggc tcgggccccg agcgtctcgg ccaagccggg gccggcgctg    1200
tggcccctgc cgctctcggt gaagatgacc ccgaacctgc tgcatctcgc cccggagaac    1260
ttctacatca gccacagccc caattccacg gcgggcccct cctgcaccct gctggaggaa    1320
gcgtttcgac gatatcatgg ctatatttt  ggtttctaca agtggcatca tgaacctgct    1380
gaattccagg ctaaacccca ggttcagcaa cttcttgtct caatcaccct tcagtcagag    1440
tgtgatgctt tccccaacat atcttcagat gagtcttata ctttacttgt gaaagaacca    1500
gtggctgtcc ttaaggccaa cagagtttgg ggagcattac gaggtttaga gacctttagc    1560
cagttagttt atcaagattc ttatggaact ttcaccatca atgaatccac cattattgat    1620
tctccaaggt tttctcacag aggaattttg attgatacat ccagacatta tctgccagtt    1680
aagattattc ttaaactct  ggatgccatg gcttttaata agtttaatgt tcttcactgg    1740
cacatagttg atgaccagtc tttcccatat cagagcatca cttttcctga gttaagcaat    1800
aaaggaagct attctttgtc tcatgtttat acaccaaatg atgtccgtat ggtgattgaa    1860
tatgccagat tacgaggaat tcgagtcctg ccagaatttg atacccctgg gcatacacta    1920
tcttggggaa aaggtcagaa agacctcctg actccatgtt acagtagaca aaacaagttg    1980
```

FIG. 1C

```
gactcttttg gacctataaa ccctactctg aatacaacat acagcttcct tactacattt  2040
ttcaaagaaa ttagtgaggt gtttccagat caattcattc atttgggagg agatgaagtg  2100
gaatttaaat gttgggaatc aaatccaaaa attcaagatt tcatgaggca aaaaggcttt  2160
ggcacagatt ttaagaaact agaatctttc tacattcaaa aggttttgga tattattgca  2220
accataaaca aggatccat tgtctggcag gaggttttg atgataaagc aaagcttgcg  2280
cgggcacaa tagttgaagt atggaaagac agcgcatatc tgaggaact cagtagagtc  2340
acagcatctg gcttccctgt aatcttct gctccttggt acttagattt gattagctat  2400
ggacaagatt ggaggaaata ctataaagtg gaacctcttg attttggcgg tactcagaaa  2460
cagaaacaac ttttcattgg tggagaagct tgtctatggg gagaatatgt ggatgcaact  2520
aacctcactc caagattatg gcctcgggca agtgctgttg gtgagagact ctggagttcc  2580
aaagatgtca gagatatgga tgacgcctat gacagactga caaggcaccg ctgcaggatg  2640
gtcgaacgtg aatagctgc acaacctctt tatgctggat attgtaacca tgagaacatg  2700
ggaagcggag ctactaactt cagcctgctg aagcaggctg gagacgtgga ggagaaccct  2760
ggacctatga caagctccag gctttggttt tcgtgctgc tgcggcagc gttcgcagga  2820
cgggcgacgg ccctctggcc ctggcctcag aacttccaaa cctccgacca gcgctacgtc  2880
ctttacccga acaactttca attccagtac gatgtcagct cggccgcgca gcccggctgc  2940
tcagtcctcg acgaggcctt ccagcgctat cgtgacctgc ttttcggttc cgggtcttgg  3000
ccccgtcctt acctcacagg gaaacggcat acactggaga agaatgtgtt ggttgtctct  3060
gtagtcacac ctggatgtaa ccagcttcct actttggagt cagtggagaa ttatccctg  3120
accataaatg atgaccagtg tttactcctc tctgagactg tctgggagc tctccgaggt  3180
ctggagactt ttagccagct tgtttggaaa tctgctgagg gcacattctt tatcaacaag  3240
actgagattg aggactttcc ccgcttcct caccggggct tgctgttgga tacatctcgc  3300
cattacctgc cactctctag catcctggac actctggatg tcatggcgta caataaattg  3360
aacgtgttcc actggcatct ggtagatgat cctttcttcc catatgagag cttcactttt  3420
ccagagctca tgagaaaggg gtcctacaac cctgtcaccc acatctacac agcacaggat  3480
gtgaaggagg tcattgaata cgcacggctc cgggtatcc gtgtgcttgc agagtttgac  3540
actctggcc acactttgtc ctggggacca ggtatcctg gattactgac tccttgctac  3600
tctgggtctg agccctctgg caccttgga ccagtgaatc ccagtctcaa taataacctat  3660
gagttcatga gcacattctt cttagaagtc agctctgtct tccagattt ttatcttcat  3720
cttggaggag atgaggttga tttcacctgc tggaagtcca acccagagat ccaggacttt  3780
atgaggaaga aaggcttcgg tgaggacttc aagcagctgg agtccttcta catccagacg  3840
ctgctggaca tctgtctcttc ttatggcaag ggctatgtgg tgtggcagga ggtgtttgat  3900
aataaagtaa agattcagcc agacacaatc atacaggtgt ggcgagagga tattccagtg  3960
```

FIG. 1C (cont'd)

```
aactatatga agqagctgga actggtcacc aaggccggct tccggccct tctctctgcc    4020
ccctggtacc tgaaccgtat atcctatggc cctgactgga aggattcta cgtagtggaa    4080
ccctggcat ttgaaggtac ccctgagcag aagctctgg tgattggtgg agaggcttgt    4140
atgtggggag aatatgtgga caacacaaac ctggtccca ggtctggcc cagagcaggg    4200
gctgttgccg aaaggctgtg gagcaacaag ttgacatctg acctgacatt tgcctatgaa    4260
cgtttgtcac acttccgctg tgagttgctg aggcgaggtg tccaggccca acccctcaat    4320
gtaggcttct gtgagcagga gtttgaacag acctgatggc cgcttcgagc agacatgata    4380
agatacattg atgagtttgg acaaccaca actagaatgc agtgaaaaaa atgctttatt    4440
tgtgaaattt gtgatgctat tgctttattt gtaaccatta taagctgcaa taaacaagtt    4500
aacaacaaca attgcattca ttttatgttt caggttcagg gggagatgtg ggaggttttt    4560
taaagcaagt aaaacctcta caaatgtggt aaaatcgata aggatcttcc tagagcatgg    4620
ctacgtagat aagtagcatg gcggttaat cattaactac aaggaaccc tagtgatgga    4680
gttggccact ccctctctgc gcgctcgctc gctcactgag gccgggcgac caaaggtcgc    4740
ccgacgcccg ggctttgccc gggcggcctc agtgagcgag cgagcgcgca gctgcattaa    4800
tgaatcggcc aacgcgcggg gagaggcggt ttgcgtattg ggcgctcttc cgcttcctcg    4860
ctcactgact cgctgcgctc ggtcgttcgg ctgcggcgag cggtatcagc tcactcaaag    4920
gcggtaatac ggttatccac agaatcaggg gataacgcag gaaagaacat gtgagcaaaa    4980
ggccagcaaa aggccaggaa ccgtaaaaag gccgcgttgc tggcgttttt ccataggctc    5040
cgcccccctg acgagcatca caaaaatcga cgctcaagtc agaggtggcg aaacccgaca    5100
ggactataaa gataccaggc gtttccccct ggaagctccc tcgtgcgctc tcctgttccg    5160
accctgccgc ttaccggata cctgtccgcc tttctccctt cggaagcgt ggcgctttct    5220
catagctcac gctgtaggta tctcagttcg gtgtaggtcg ttcgctccaa gctgggctgt    5280
gtgcacgaac cccccgttca gcccgaccgc tgcgccttat ccggtaacta tcgtcttgag    5340
tccaacccgg taagacacga cttatcgcca ctggcagcag ccactggtaa caggattagc    5400
agagcgaggt atgtaggcgg tgctacagag ttcttgaagt ggtggcctaa ctacggctac    5460
actagaagaa cagtatttgg tatctgcgct ctgctgaagc cagttaccct cggaaaaaga    5520
gttggtagct cttgatccgg caaacaaacc accgctggta gcggtggttt ttttgtttgc    5580
aagcagcaga ttacgcgcag aaaaaaggga tctcaagaag atcctttgat cttttctacg    5640
gggtctgacg ctcagtggaa cgaaaactca cgttaaggga ttttggtcat gagattatca    5700
aaaggatct tcacctagat ccttttaaat taaaatgaa gttttaaatc aatctaaagt    5760
atatatgagt aaacttggtc tgacagttac caatgcttaa tcagtgaggc acctatctca    5820
gcgatctgtc tatttcgttc atccatagtt gcctgactcc ccgtcgtgta gataactacg    5880
atacgggagg gcttaccatc tggccccagt gctgcaatga taccgcgaga cccacgctca    5940
```

FIG. 1C (cont'd)

```
ccggctccag atttatcagc aataaaccag ccagccggaa gggccgagcg cagaagtggt    6000
cctgcaactt tatccgcctc catccagtct attaattgtt gccgggaagc tagagtaagt    6060
agttcgccag ttaatagttt cgcaacgtt gttgccattg ctacaggcat cgtggtgtca    6120
cgctcgtcgt ttggtatggc ttcattcagc tccggttccc aacgatcaag gcgagttaca    6180
tgatccccca tgttgtgcaa aaagcggtt agctcttcg gtcctccgat cgttgtcaga    6240
agtaagttgg ccgcagtgtt atcactcatg gttatggcag cactgcataa ttctcttact    6300
gtcatgccat ccgtaagatg cttttctgtg actggtgagt actcaaccaa gtcattctga    6360
gaatagtgta tgcggcgacc gagttgctct tgcccggcgt caatacggga taataccgcg    6420
ccacatagca gaactttaaa agtgctcatc attggaaaac gttcttcggg gcgaaaactc    6480
tcaaggatct taccgctgtt gagatccagt tcgatgtaac ccactcgtgc acccaactga    6540
tcttcagcat cttttacttt caccagcgtt tctgggtgag caaaaacagg aaggcaaaat    6600
gccgcaaaaa agggaataag ggcgacacgg aaatgttgaa tactcatact cttccttttt    6660
caatattatt gaagcattta tcaggttat tgtctcatga gcggatacat atttgaatgt    6720
atttagaaaa ataaacaaat aggggttccg cgcacatttc ccgaaaagt gccacctaaa    6780
ttgtaagcgt taatattttg ttaaaattcg cgttaaattt ttgttaaatc agctcatttt    6840
ttaaccaata ggccgaaatc ggcaaaatcc cttataaatc aaaagaatag accgagatag    6900
ggttgagtgt tgttccagtt tggaacaaga gtccactatt aaagaacgtg gactccaacg    6960
tcaaagggcg aaaaaccgtc tatcagggcg atggcccact acgtgaacca tcacctaat    7020
caagtttttt ggggtcgagg tgccgtaaag cactaaatcg gaaccctaaa gggagccccc    7080
gatttagagc ttgacgggga agccggcga acgtggcgag aaaggaaggg aagaaagcga    7140
aaggagcggg cgctagggcg ctggcaagtg tagcggtcac gctgcgcgta accaccacac    7200
ccgccgcgct taatgcgccg ctacaggcg cgtcccattc gccattcagg ctgcgcaact    7260
gttgggaagg gcgatcggtg cgggcctctt cgctattacg cca                     7303
```

FIG. 1C (cont'd)

| PART OF CONSTRUCT | | NUCLEOTIDE NUMBERING (SEQ ID NO:1) |
|---|---|---|
| ITR | | 1-188 |
| CMV | | 194-463 |
| CB | | 439-720 |
| Chicken Beta actin promoter | | 442-719 |
| b-actin intron | | 720-950 |
| hHEXBP2AHEXA | | 1028-4361 |
| | HEXB | 1028-2709 |
| | P2A | 2710-2766 |
| | HEXA | 2767-4361 |
| SV40 poly(A) signal | | 4379-4500 |
| ITR | | 4605-4792 |
| Ori | | 5028-5616 |
| AmpR | | 5787-6647 |
| AmpR promoter | | 6648-6752 |
| f1 ori | | 6778-7303 |

FIG. 1D

SEQUENCE LISTING

```
<160> NUMBER OF SEQ ID NOS: 1

<210> SEQ ID NO 1
<211> LENGTH: 7303
<212> TYPE: DNA
<213> ORGANISM: Artificial Sequence
<220> FEATURE:
<223> OTHER INFORMATION: Synthetic Construct

<400> SEQUENCE: 1
gctgcgcgct cgctcgctca ctgaggccgc ccgggcaaag cccgggcgtc gggcgacctt       60
tggtcgcccg gcctcagtga gcgagcgagc gcgcagagag ggagtggcca actccatcac      120 tagggttcc ttgtagttaa tgattaaccc gccatgctac ttatctacgt agccatgctc       180
taggaagagt accattgacg tcaataatga cgtatgttcc catagtaacg ccaataggga      240
ctttccattg acgtcaatgg gtggagtatt tacggtaaac tgcccacttg gcagtacatc      300
aagtgtatca tatgccaagt acgccccta ttgacgtcaa tgacggtaaa tggcccgcct       360
ggcattatgc ccagtacatg accttatggg actttcctac ttggcagtac atctacgtat      420
tagtcatcgc tattaccatg gtcgaggtga gccccacgtt ctgcttcact ctccccatct      480 cccccctc cccaccccca attttgtatt tatttatttt ttaattattt tgtgcagcga        540
tgggggcggg gggggggggg gggcgcgcgc caggcggggc gggcggggc gaggggcggg       600 gcggggcgag gcggagaggt gcggcggcag ccaatcagag cggcgcgctc cgaaagtttc      660
```

```
cttttatggc gaggcggcgg cggcggcggc cctataaaaa gcgaagcgcg cggcgggcgg      720
gagtcgctgc gcgctgcctt cgccccgtgc cccgctccgc cgccgcctcg cgccgcccgc      780
cccggctctg actgaccgcg ttactcccac aggtgagcgg gcgggacggc ccttctcctc      840
cgggctgtaa ttagcgcttg gtttaatgac ggcttgtttc ttttctgtgg ctgcgtgaaa      900
gccttgaggg gctccgggag ggccctttgt gcgggggggag cggctcgggg ctgtccgcgg      960
ggggacggct gccttcgggg gggacgggggc agggcgggggt tcggcttctg gcgtgtgacc     1020
ggcggctcta gaatggagct gtgcgggctg gggctgcccc ggccgcccat gctgctggcg     1080
ctgctgttgg cgacactgct ggcggcgatg ttggcgctgc tgactcaggt ggcgctggtg     1140
gtgcaggtgg cggaggcggc tcgggccccg agcgtctcgg ccaagccggg gccggcgctg     1200
tggcccctgc cgctctcggt gaagatgacc ccgaacctgc tgcatctcgc cccggagaac     1260
ttctacatca gccacagccc caattccacg gcgggcccct cctgcaccct gctggaggaa     1320
gcgtttcgac gatatcatgg ctatatttt ggtttctaca gtggcatca tgaacctgct     1380 gaattccagg ctaaaaccca ggttcagcaa cttcttgtct caatcaccct tcagtcagag     1440
tgtgatgctt tccccaacat atcttcagat gagtcttata ctttacttgt gaaagaacca     1500
gtggctgtcc ttaaggccaa cagagtttgg ggagcattac gaggtttaga gacctttagc     1560
cagttagttt atcaagattc ttatggaact ttcaccatca tgaatccac cattattgat     1620 tctccaaggt tttctcacag aggaattttg attgatacat ccagacatta tctgccagtt     1680
aagattattc ttaaaactct ggatgccatg gcttttaata agtttaatgt tcttcactgg     1740
cacatagttg atgaccagtc tttcccatat cagagcatca cttttcctga gttaagcaat     1800
aaaggaagct attctttgtc tcatgtttat acaccaaatg atgtccgtat ggtgattgaa     1860
tatgccagat tacgaggaat tcgagtcctg ccagaatttg ataccctgg gcatacacta     1920 tcttggggaa aaggtcagaa agacctcctg actccatgtt acagtagaca aaacaagttg     1980
gactcttttg gacctataaa ccctactctg aatacaacat acagcttcct tactacattt     2040
ttcaaagaaa ttagtgaggt gtttccagat caattcattc atttgggagg agatgaagtg     2100
gaatttaaat gttgggaatc aaatccaaaa attcaagatt tcatgaggca aaaaggcttt     2160
ggcacagatt ttaagaaact agaatctttc tacattcaaa aggttttgga tattattgca     2220
accataaaca agggatccat tgtctggcag gaggttttttg atgataaagc aaagcttgcg     2280
ccgggcacaa tagttgaagt atggaaagac agcgcatatc ctgaggaact cagtagagtc     2340
acagcatctg gcttccctgt aatcctttct gctccttggt acttagattt gattagctat     2400
ggacaagatt ggaggaaata ctataaagtg gaacctcttg attttggcgg tactcagaaa     2460
cagaaacaac ttttcattgg tggagaagct tgtctatggg gagaatatgt ggatgcaact     2520
aacctcactc caagattatg gcctcgggca agtgctgttg gtgagagact ctggagttcc     2580
aaagatgtca gagatatgga tgacgccatt gacagactga caaggcaccg ctgcaggatg     2640
gtcgaacgtg gaatagctgc acaacctctt tatgctggat attgtaacca tgagaacatg     2700
ggaagcggag ctactaactt cagcctgctg aagcaggctg gagacgtgga ggagaaccct     2760
ggacctatga caagctccag gctttggttt tcgctgctgc tggcggcagc gttcgcagga     2820
cgggcgacgg ccctctggcc ctggcctcag aacttccaaa cctccgacca gcgctacgtc     2880
ctttacccga caaactttca attccagtac gatgtcagct cggccgcgca gcccggctgc     2940
tcagtcctcg acgaggcctt ccagcgctat cgtgacctgc ttttcggttc cgggtcttgg     3000
```

```
ccccgtcctt acctcacagg gaaacggcat acactggaga agaatgtgtt ggttgtctct    3060
gtagtcacac ctggatgtaa ccagcttcct actttggagt cagtggagaa ttatacccctg   3120
accataaatg atgaccagtg tttactcctc tctgagactg tctggggagc tctccgaggt    3180
ctggagactt ttagccagct tgtttggaaa tctgctgagg gcacattctt tatcaacaag    3240
actgagattg aggactttcc ccgctttcct caccggggct tgctgttgga tacatctcgc    3300
cattacctgc cactctctag catcctggac actctggatg tcatggcgta caataaattg    3360
aacgtgttcc actggcatct ggtagatgat ccttccttcc catatgagag cttcactttt    3420
ccagagctca tgagaaaggg gtcctacaac cctgtcaccc acatctacac agcacaggat    3480
gtgaaggagg tcattgaata cgcacggctc cggggtatcc gtgtgcttgc agagtttgac    3540
actcctggcc acactttgtc ctggggacca ggtatccctg gattactgac tccttgctac    3600
tctgggtctg agccctctgg caccttttgga ccagtgaatc ccagtctcaa taatacctat   3660
gagttcatga gcacattctt cttagaagtc agctctgtct tcccagattt ttatcttcat    3720
cttggaggag atgaggttga tttcacctgc tggaagtcca acccagagat ccaggacttt    3780
atgaggaaga aaggcttcgg tgaggacttc aagcagctgg agtccttcta catccagacg    3840
ctgctggaca tcgtctcttc ttatggcaag ggctatgtgg tgtggcagga ggtgtttgat    3900
aataaagtaa agattcagcc agacacaatc atacaggtgt ggcgagagga tattccagtg    3960
aactatatga aggagctgga actggtcacc aaggccggct tccgggccct tctctctgcc    4020
ccctggtacc tgaaccgtat atcctatggc cctgactgga aggatttcta cgtagtggaa    4080
cccctggcat ttgaaggtac ccctgagcag aaggctctgg tgattggtgg agaggcttgt    4140
atgtggggag aatatgtgga caacacaaac ctggtcccca ggctctggcc cagagcaggg    4200
gctgttgccg aaaggctgtg gagcaacaag ttgacatctg acctgacatt tgcctatgaa    4260
cgtttgtcac acttccgctg tgagttgctg aggcgaggtg tccaggccca accccctcaat   4320
gtaggcttct gtgagcagga gtttgaacag acctgatggc cgcttcgagc agacatgata    4380
agatacattg atgagtttgg acaaaccaca actagaatgc agtgaaaaaa atgctttatt    4440
tgtgaaattt gtgatgctat tgcttttattt gtaaccatta taagctgcaa taaacaagtt    4500
aacaacaaca attgcattca ttttatgttt caggttcagg gggagatgtg ggaggttttt    4560
taaagcaagt aaaacctcta caaatgtggt aaaatcgata aggatcttcc tagagcatgg    4620
ctacgtagat aagtagcatg gcgggttaat cattaactac aaggaacccc tagtgatgga    4680
gttggccact ccctctctgc gcgctcgctc gctcactgag gccgggcgac caaaggtcgc    4740
ccgacgcccg ggctttgccc gggcggcctc agtgagcgag cgagcgcgca gctgcattaa    4800
tgaatcggcc aacgcgcggg gagaggcggt ttgcgtattg ggcgctcttc cgcttcctcg    4860
ctcactgact cgctgcgctc ggtcgttcgg ctgcggcgag cggtatcagc tcactcaaag    4920
gcggtaatac ggttatccac agaatcaggg gataacgcag gaaagaacat gtgagcaaaa    4980
ggccagcaaa aggccaggaa ccgtaaaaag gccgcgttgc tggcgttttt ccataggctc    5040
cgcccccctg acgagcatca caaaaatcga cgctcaagtc agaggtggcg aaacccgaca    5100
ggactataaa gataccaggc gtttccccct ggaagctccc tcgtgcgctc tcctgttccg    5160
accctgccgc ttaccggata cctgtccgcc tttctccctt cgggaagcgt ggcgctttct    5220
catagctcac gctgtaggta tctcagttcg gtgtaggtcg ttcgctccaa gctgggctgt    5280
gtgcacgaac ccccgttca gcccgaccgc tgcgccttat ccggtaacta tcgtcttgag    5340
tccaacccgg taagacacga cttatcgcca ctggcagcag ccactggtaa caggattagc    5400
```

```
agagcgaggt atgtaggcgg tgctacagag ttcttgaagt ggtggcctaa ctacggctac    5460
actagaagaa cagtatttgg tatctgcgct ctgctgaagc cagttacctt cggaaaaaga    5520
gttggtagct cttgatccgg caaacaaacc accgctggta gcggtggttt ttttgtttgc    5580
aagcagcaga ttacgcgcag aaaaaaagga tctcaagaag atcctttgat cttttctacg    5640
gggtctgacg ctcagtggaa cgaaaactca cgttaaggga ttttggtcat gagattatca    5700
aaaaggatct tcacctagat ccttttaaat taaaaatgaa gttttaaatc aatctaaagt    5760
atatatgagt aaacttggtc tgacagttac caatgcttaa tcagtgaggc acctatctca    5820
gcgatctgtc tatttcgttc atccatagtt gcctgactcc ccgtcgtgta gataactacg    5880
atacgggagg gcttaccatc tggccccagt gctgcaatga taccgcgaga cccacgctca    5940
ccggctccag atttatcagc aataaaccag ccagccggaa gggccgagcg cagaagtggt    6000
cctgcaactt tatccgcctc catccagtct attaattgtt gccgggaagc tagagtaagt    6060
agttcgccag ttaatagttt gcgcaacgtt gttgccattg ctacaggcat cgtggtgtca    6120
cgctcgtcgt ttggtatggc ttcattcagc tccggttccc aacgatcaag gcgagttaca    6180
tgatccccca tgttgtgcaa aaaagcggtt agctccttcg gtcctccgat cgttgtcaga    6240
agtaagttgg ccgcagtgtt atcactcatg gttatggcag cactgcataa ttctcttact    6300
gtcatgccat ccgtaagatg cttttctgtg actggtgagt actcaaccaa gtcattctga    6360
gaatagtgta tgcggcgacc gagttgctct tgcccggcgt caatacggga taataccgcg    6420
ccacatagca gaactttaaa agtgctcatc attggaaaac gttcttcggg gcgaaaactc    6480
tcaaggatct taccgctgtt gagatccagt tcgatgtaac ccactcgtgc acccaactga    6540
tcttcagcat cttttacttt caccagcgtt tctgggtgag caaaaacagg aaggcaaaat    6600
gccgcaaaaa agggaataag ggcgacacgg aaatgttgaa tactcatact cttccttttt    6660
caatattatt gaagcattta tcagggttat tgtctcatga gcggatacat atttgaatgt    6720
atttagaaaa ataaacaaat aggggttccg cgcacatttc cccgaaaagt gccacctaaa    6780
ttgtaagcgt taatattttg ttaaaattcg cgttaaattt ttgttaaatc agctcatttt    6840
ttaaccaata ggccgaaatc ggcaaaatcc cttataaatc aaaagaatag accgagatag    6900
ggttgagtgt tgttccagtt tggaacaaga gtccactatt aaagaacgtg gactccaacg    6960
tcaaagggcg aaaaaccgtc tatcagggcg atggcccact acgtgaacca tcaccctaat    7020 caagttttt ggggtcgagg tgccgtaaag cactaaatcg gaaccctaaa gggagccccc    7080
gatttagagc ttgacgggga agccggcga acgtggcgag aaaggaaggg aagaaagcga    7140
aaggagcggg cgctagggcg ctggcaagtg tagcggtcac gctgcgcgta accaccacac    7200
ccgccgcgct taatgcgccg ctacagggcg cgtcccattc gccattcagg ctgcgcaact    7260
gttgggaagg gcgatcggtg cgggcctctt cgctattacg cca                     7303
```

METHODS AND GENE THERAPY CONSTRUCTS FOR TREATING GM2 GANGLIOSIDOSES

RELATED APPLICATION

This application claims the benefit of the filing date of Application No. 62/348,003, filed Jun. 9, 2016, and is a continuation of application Ser. No. 15/617,465, now U.S. Pat. No. 11,045,557, the contents of which are incorporated herein in their entirety.

FIELD

This invention relates to nucleic acid constructs containing both HexA and HexB encoding genetic elements. Such constructs can be used for gene therapy treatment of individuals with deficiencies of β-hexosaminidase A protein expression or activity including, but not limited to, Sandhoff disease and Tay-Sach's disease. Also described are complimentary drug treatments that enhance the gene therapy treatment.

BACKGROUND

GM2 gangliosidoses is a group of fatal, autosomal recessive, lysosomal storage disorders caused by a deficiency in β-hexosaminidase A (HexA) enzyme expression or activity. HexA is a heterodimer composed of 2 subunits; β-hexosaminidase a (encoded by the HEXA gene) and β-hexosaminidase β (encoded by the HEXB gene). HexA is essential for the degradation of GM2 gangliosides in the cell's lysosome. Mutations in either the HEXA or HEXB gene may cause inactivity of HexA, allowing glycolipid intermediates to build up within the central nervous system (CNS). This results in inflammation, cell death, and neurodegeneration.

The most common forms of GM2 gangliosidoses are Tay Sach's disease (TSD) and Sandhoff disease (SD). Tay Sach's disease, which is the result of mutations in the HEXA gene, has a carrier frequency of 1 in 25 individuals of Ashkenazi Jewish descent. Sandhoff disease, which results from mutations in the HEXB gene, has an incidence of 1 in 384,000 live births, but is increased in some populations including French Canadian. Principally affecting young children, Tay Sach's and Sandhoff diseases result in clinically indistinguishable disease phenotypes for which there is no effective treatment.

One relevant consequence of GM2 buildup in the brain, which is observed in both humans and mouse models of SD, is an extensive inflammatory response. This inflammatory response is characterized by microglial activation, macrophage recruitment, and proinflammatory cytokine production throughout the CNS, and there is also evidence for extensive oxidative damage. Examination of the temporal relationship has shown that microglial activation precedes acute neurodegeneration in the mouse model of SD along with at least one human case of SD. An important question is whether inflammation directly contributes to disease progression and could then be a target of therapy. The prevailing model represents inflammation as a response to initial neuronal insult by GM2 ganglioside build-up, the inflammatory response then causes further neuronal damage and further inflammation. This would suggest inflammation would contribute directly to the disease progression.

Mouse models for both Tay Sach's disease and Sandhoff disease (SD) have been developed and characterized through the targeted disruption of the murine HEXA and HEXB genes respectively. Mutations in the HEXA gene surprisingly resulted in a late onset form due to an alternative metabolic pathway found in mice. Mutations in the HEXB gene, however, resulted in a severe phenotype similar to infant onset SD or TSD characterized by extensive GM2 ganglioside accumulation in the brain and spinal cord. Similar to the human phenotype, these mice appear healthy at birth followed by a rapid and fatal neurodegeneration beginning at about 3 months of age with humane end points typically at 15-17 weeks. Spasticity, muscle weakness, rigidity, and lack of purposeful movement leading to immobility are all typical of disease progression. These mice have been used extensively as a model for studying potential therapies for the GM2 gangliosidoses (Sandhoff and Harzer, 2013).

SUMMARY

According to one aspect, the invention provides nucleic acid constructs containing both HexA and HexB encoding elements in a single vector, and related methods, for treating GM2 gangliosidoses such as Sandhoff disease and Tay-Sach's disease, by gene therapy.

According to this aspect, there is provided a composition, comprising: a vector; a promoter; a nucleotide sequence encoding a HEXB gene and a nucleotide sequence encoding a HEXA gene; and a nucleotide sequence encoding a self-cleaving peptide that links the HEXB gene and the HEXA gene. The vector may comprise an AAV plasmid selected from AAV serotypes 1, 2, 3, 4, 5, 6, 7, 8, 9, and rh10. In one embodiment, the vector comprises an AAV9 plasmid. In one embodiment, the promoter comprises a CAG promoter. In one embodiment, the nucleotide sequence encoding a self-cleaving peptide encodes a P2A linker. In one embodiment the composition comprises the construct of SEQ ID NO:1, or a functional equivalent thereof.

The composition may comprise a therapeutically effective amount of at least one anti-inflammatory agent, or at least one pharmaceutical chaperone agent, or a combination thereof. The at least one anti-inflammatory agent may comprise at least one agent selected from indomethacin and ITF2357. The at least one pharmacological chaperone agent may comprise pyrimethamine.

The composition may be suitable for systemic administration to a subject, or for intravenous administration to a subject. The composition may be for use in enhancing β-hexosaminidase A (HexA) enzyme activity in a subject in need thereof. The subject may be predisposed to having, suspected of having, or diagnosed as having a lysosomal storage disorder characterized by a deficiency in HexA expression or activity. The HexA deficiency may comprise a partial or complete loss of endogenous expression or function of β-hexosaminidase a (encoded by the HEXA gene), β-hexosaminidase β (encoded by the HEXB gene), or both. The HexA deficiency may comprise Tay-Sach's disease or Sandhoff disease. The composition may be for use in treating, reducing the severity of, or delaying the onset of Tay-Sach's disease and/or Sandhoff disease.

In various embodiments the constructs may be used for gene therapy treatment of individuals with deficiencies of β-hexosaminidase A protein (HexA) expression or activity including Sandhoff disease, Tay-Sach's disease, Alzheimer's disease, Parkinson's disease, ALS, and other dementia-related disorders.

Thus, according to another aspect, the invention provides a method for enhancing β-hexosaminidase A (HexA) enzyme activity in a subject in need thereof, comprising:

administering to the subject a therapeutically effective amount of a composition comprising an expression construct comprising; a vector; a promoter; a nucleotide sequence encoding a HEXB gene and a nucleotide sequence encoding a HEXA gene; and a nucleotide sequence encoding a self-cleaving peptide that links the HEXB gene and the HEXA gene. The vector may comprise an 0.3-. AAV plasmid selected from AAV serotypes 1, 2, 3, 4, 5, 6, 7, 8, 9, and rh10. In one embodiment, the vector comprises an AAV9 plasmid.

In accordance with this aspect, the subject may be predisposed to having, suspected of having, or diagnosed as having a lysosomal storage disorder characterized by a deficiency in HexA expression or activity. The HexA deficiency may comprise a partial or complete loss of endogenous expression or function of β-hexosaminidase a (encoded by the HEXA gene), β-hexosaminidase p (encoded by the HEXB gene), or both. The HexA deficiency may comprise Tay-Sach's disease or Sandhoff disease.

In various embodiments, the method may comprise treating, reducing the severity of, or delaying the onset of Tay-Sach's disease and/or Sandhoff disease. The method may comprise administering the composition to the subject systemically or intravenously.

The method may comprise administering a composition comprising the construct of SEQ ID NO:1, or a functional equivalent thereof. The method may comprise administering a composition comprising a therapeutically effective amount of at least one anti-inflammatory agent, or at least one pharmaceutical chaperone agent, or a combination thereof. The at least one anti-inflammatory agent may comprise at least one agent selected from indomethacin and ITF2357. The at least one pharmaceutical chaperone agent may comprise pyrimethamine.

In accordance with the aspects and embodiments of the invention, the subject may be human.

BRIEF DESCRIPTION OF FIGURES

For a greater understanding of the invention, and to show more clearly how it may be carried into effect, embodiments will be described, by way of example, with reference to the accompanying drawings, wherein:

FIG. 1C shows the nucleic acid sequence of an AAV9 HEXB-HEXA vector construct, according to one embodiment, referred to as SEQ ID NO:1.

FIG. 1D is a table showing nucleotide numbering for parts of the construct of FIGS. 1B and 1C.

DETAILED DESCRIPTION OF EMBODIMENTS

Figure 1A:
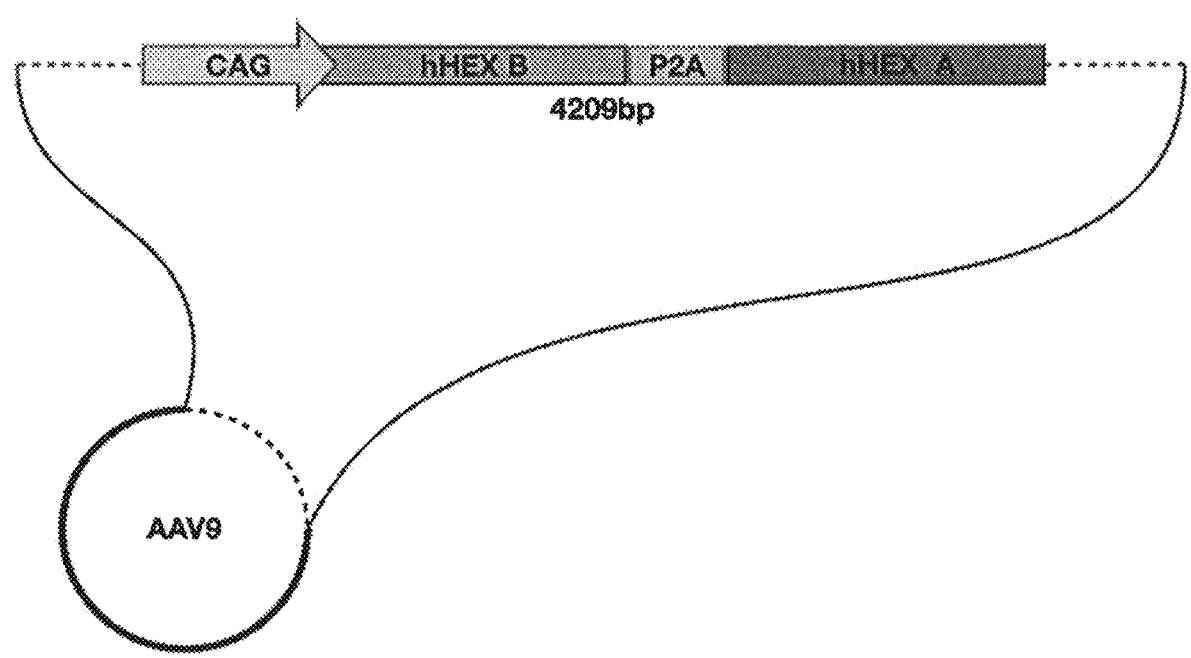
FIG. 1A is a diagram showing an AAV9 HEXB-HEXA vector construct, according to one embodiment.

This disclosure relates generally to constructs and methods for the treatment of lysosomal storage disorders with adeno-associated virus (AAV)-mediated gene therapy. In particular, this disclosure provides constructs and methods for treating, reducing the severity of, or delaying the onset of Tay-Sach's disease and Sandhoff disease by providing AAV-mediated HexA expression in the brain of a subject in need thereof. AAV-mediated HexA expression is achieved by administering pharmaceutical compositions comprising AAV-HexA expression constructs to a subject. In practicing the embodiments described herein, many conventional techniques in cell biology, molecular biology, protein biochemistry, immunology, and bacteriology are used. These techniques are well-known in the art and are provided in any number of available publications, including Current Protocols in Molecular Biology, Vols. I-III, Ausubel, Ed. (1997); Sambrook et al., Molecular Cloning: A Laboratory Manual, Second Ed. (Cold Spring Harbor Laboratory Press, Cold Spring Harbor, N.Y., 1989). Unless specifically defined herein, all technical and scientific terms used herein generally have the same meaning as commonly understood by one of ordinary skill in the art to which this invention belongs. A number of AAV serotypes are known and well-described in the art. Embodiments described herein may employ any of AAV serotypes 1, 2, 3, 4, 5, 6, 7, 8, 9, and rh10. Nucleotide sequences of these serotypes are readily available, and, for the sake of brevity, are not provided herein. An embodiment is described herein based on serotype AAV9; however, it will be understood that other serotypes may also be used. Thus, for example, as used herein, "AAV9 vector" refers to an AAV vector carrying the adeno-associated virus isolate AAV9 capsid protein (VP1) gene.

The term "gene therapy" as used herein means genetic modification of cells by the introduction of exogenous DNA or RNA into these cells for the purpose of expressing or replicating one or more peptides, polypeptides, proteins, oligonucleotides, or polynucleotides in vivo for the treatment or prevention of disease or deficiencies in humans or animals. Gene therapy is generally disclosed in U.S. Pat. No. 5,399,346. Any suitable route or routes of administration of the nucleic acid or protein may be employed for providing a subject with pharmaceutical compositions of the presently disclosed inventive constructs, optionally in combination with one or more pharmaceutical agents. For example, parenteral (subcutaneous, subretinal, suprachoroidal, intramuscular, intravenous, transdermal, intracranial) and like forms of administration may be employed alone or in combination. Dosage formulations include injections, implants, or other known and effective gene therapy delivery methods.

As used herein, the term "AAV9" encompasses natural and engineered AAV9 variants. In some embodiments, variants have about 60% sequence identity, and in some embodiments 65%, 70%, 75%, 80%, 85%, 90%, 91%, 92%, 93%, 94%, 95%, 96%, 97%, 98%, 99%, or higher identity over a specified region. Similarly, natural and engineered variants of AAV serotypes 1, 2, 3, 4, 5, 6, 7, 8, and rh10 may have such sequence identity.

As used herein, the "administration" of a construct, agent, drug, or peptide, or combination thereof to a subject includes any route or routes of introducing or delivering to a subject a compound to perform its intended function. Administration can be carried out by any suitable route, including orally, intranasally, parenterally (intravenously, intramuscularly, intrathecally, epidurally, intracranially, intraperitoneally, or subcutaneously), or topically, or by a combination thereof. Parenteral administration of the composition, if used, is generally characterized by injection. Injectables can be prepared in conventional forms, either as liquid solutions or suspensions, solid forms suitable for solution of suspension in liquid prior to injection, or as emulsions. In some embodiments, "administration" refers to direct infusion of pharmaceutical compositions comprising AAV9 expression constructs by intravenous administration or injection into the brain for distribution and expression of the constructs. In some embodiments, the infusion site is chosen from the group consisting of the thalamus, striatum, deep cerebral parenchyma intravenously or into the cerebrospinal fluid. Compositions may be administered at any site within the brain sufficient to result in widespread distribution. The exact amount of the compositions required will vary from subject to subject, depending on the species, age, weight and general condition of the subject, the severity of the allergic disorder being treated, the particular nucleic acid or vector used, its mode of administration and the like. Thus, it is not possible to specify an exact amount for every composition. However, an appropriate amount can be determined by one of ordinary skill in the art using only routine experimentation given the teachings herein.

As used herein, the term "effective amount" or "pharmaceutically effective amount" or "therapeutically effective amount" or "prophylactically effective amount" of a composition is a quantity sufficient to achieve or maintain a desired therapeutic and/or prophylactic effect, e.g., an amount which results in the prevention of, or a decrease in, the symptoms associated with a disease that is being treated, e.g., of a lysosomal storage disorder.

As used herein, the terms "isolate" and "purify" refer to processes of obtaining a biological substance that is substantially free of material and/or contaminants normally found in its natural environment (e.g., from the cells or tissues from which a protein is derived, or substantially free from chemical precursors or other chemicals when chemically synthesized).

As used herein, "expression" includes, but is not limited to one or more of the following: transcription of the gene into precursor mRNA; splicing and other processing of the precursor mRNA to produce mature mRNA; mRNA stability; translation of the mature mRNA into protein (including codon usage and tRNA availability); and glycosylation and/or other modifications of the translation product, if required for proper expression and function.

As described above, the compositions can also be administered in vivo in a pharmaceutically acceptable carrier. By "pharmaceutically acceptable" is meant a material that is not biologically or otherwise undesirable, i.e., the material may be administered to a subject, along with the nucleic acid or vector, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

As used herein, the term "pharmaceutically-acceptable carrier" is intended to include any and all solvents, dispersion media, coatings, antibacterial and antifungal compounds, isotonic and absorption delaying compounds, and the like, compatible with pharmaceutical administration. Suitable carriers and their formulations are described in Remington: The Science and Practice of Pharmacy (19th ed.) ed. A. R. Gennaro, Mack Publishing Company, Easton, Pa. 1995. Typically, an appropriate amount of a pharmaceutically-acceptable salt is used in the formulation to render the formulation isotonic. Examples of the pharmaceutically-acceptable carrier include, but are not limited to, saline, Ringer's solution, and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes, or microparticles. It will be apparent to those persons skilled in the art that certain carriers may be more preferable depending upon, for instance, the route of administration and concentration of composition being administered.

As used herein, the term "polynucleotide" or "nucleic acid" means any RNA or DNA, which may be unmodified or modified RNA or DNA. Polynucleotides include, without limitation, single- and double-stranded DNA, DNA that is a mixture of single- and double-stranded regions, single- and double-stranded RNA, RNA that is mixture of single- and double-stranded regions, and hybrid molecules comprising DNA and RNA that may be single-stranded or, more typically, double-stranded or a mixture of single- and double-stranded regions. In addition, polynucleotide refers to triple-stranded regions comprising RNA or DNA or both RNA and DNA. The term polynucleotide also includes DNAs or RNAs containing one or more modified bases and DNAs or RNAs with backbones modified for stability or for other reasons. The term encompasses any base analogue of DNA and RNA.

The term DNA "control sequences" includes but is not limited to promoter sequences such as neuronal promoter sequences, e.g., synapsyn (SYN), synapsin 1, CamkII, MeCP2, Hb9, neuronal-specific enolase (NSE) promoter, CMV, and CAG, polyadenylation signals, transcription termination sequences, upstream regulatory domains, origins of replication, internal ribosome entry sites ("IRES"), 2A linkers including but not limited to porcine teschovirus-1 2A (P2A), enhancers, and the like, which collectively provide for the replication, transcription and translation of a coding sequence in a recipient cell. Not all of these control sequences need always be present so long as the selected coding sequence is capable of being replicated, transcribed and translated in an appropriate host cell.

Embodiments described herein provide constructs and methods for enhancing β-hexosaminidase A (HexA) enzyme activity in a subject in need thereof, comprising administering to the subject a therapeutically effective amount of a composition comprising an expression construct comprising a vector, a promoter, a nucleotide sequence encoding a HEXB gene and a nucleotide sequence encoding a HEXA gene, and a nucleotide sequence encoding a self-cleaving peptide that links the HEXB gene and the HEXA gene. Embodiments optionally include co-administration of one or more pharmaceutical agent, such as one or more anti-inflammatory agent. As used herein, "co-administration"

means administration at the same time, or substantially at the same time, using the same route, or using different routes.

Recent gene replacement/gene therapy experimentation has revealed the need for providing both HEXA and HEXB genes concurrently (i.e., at the same time) to achieve likely successful gene therapy treatment. Gene transfer experiments in cell culture have shown that overexpression of human α-subunit in human or mouse Tay-Sachs fibroblasts results in a significant reduction in HEXB activity likely due to depletion of the endogenous β-subunit pool. Also, gene transfer experiments in Tay-Sach's mice have shown that co-transduction with two viral vectors encoding human α- and β-subunit separately were needed to achieve high-level HexA synthesis and secretion. Therefore, effective gene therapy strategies for GM2-gangliosidoses should utilize gene delivery vehicles encoding both the α- and β-subunits, ideally through one construct. Experimental gene therapy approaches have shown promise in mouse and cat models, extending life and improving disease symptoms. Adeno-associated virus (AAV) is a vector candidate for many gene therapies. A single stranded virus with a genome size of approximately 4.7 kb and belonging to the parovirus family, AAV is not associated with any disease in humans. Recombinant AAV vectors have been utilized as effective gene delivery vehicles as they can transduce non-dividing cells and confer long-term stable gene expression.

The AAV serotype 9 (AAV9) has been shown to cross the blood brain barrier and preferentially transduce neurons in neonates and astrocytes in adults (Foust et al. 2009; Bourdenx et al. 2014). AAV9 effectively eliminates the need for direct injection into the CNS as systemic delivery should reach CNS targets. However, AAVs, including AAV9, have been considered to be limited by genome size with the limitation thought to be similar to the size of the parent AAV genome (Wu et al. 2010). Indeed, exceeding the packaging limit was noted as a possible reason for the lack of HexA expression in cell transfection experiments with AAV2 plasmid containing both HEXA and HEXB genes (Bera 2008). A number of diseases have multi-gene defects and hence a multi-gene vector approach would be the most efficient method of gene therapy. Such bicistronic or multicistronic approaches have commonly utilized internal ribosomal entry sites (IRES) that allow the ribosome to begin translation at both the beginning of the mRNA and at the IRES. IRES have limitations though due to their large size, usually 500 nucleotides, and the fact that they result in unequal expression of the two genes flanking them. Self-cleaving 2A peptides have been used to function in a similar manner, and while remaining small (18-22 amino acids long) these 2A peptides result in almost equal expression of both genes flanking the linker. While being translated, the ribosome skips the synthesis of the glycyl-prolyl peptide bond at the C-terminus of the 2A peptide, leading to a cleavage between the 2A peptide and its immediate downstream peptide. This process has been shown to be universal in all eukaryotic cells and does not rely on any proteases as was first assumed. In this way, two proteins can be transcribed under the same promoter and if a functional 2A linker separates them, the translation process will result in two distinct and independent proteins. Porcine teschovirus-1 2A (P2A) is one such 2A peptide that has become widely used in biomedical research and shows high cleavage efficiency in many in vivo conditions (Kim et al. 2011). However, bicistronic AAV2 plasmids containing both HEXA and HEXB genes with either IRES or P2A failed to produce active enzyme over control plasmids in cell transfection experiments (Bera 2008).

In addition to gene therapy approaches, a number of anti-inflammatory drug therapies have been shown to improve motor function and life expectancy to a limited degree in GM2 gangliosidoses. Non-steroidal anti-inflammatory drugs decrease the inflammation response in the CNS, and have been shown to provide a significant increase in life expectancy of 12-13% in mouse models. Another anti-inflammatory therapy approach, the use of Histone deacetylase inhibitors (HDACi), has been shown to significantly reduce immune cell activation particularly in the CNS. Since a perturbation in acetylation and inflammation is a central event leading to neuronal cell death, a pan-HDACi such as ITF2357 may provide a neuroprotective effect in neuroinflammatory conditions (Faraco et al., 2009).

Another type of drug therapy in the forefront of GM2 gangliosidoses treatment is the use of a pharmacological chaperone (PC), such as pyrimethamine (Daraprim®). PCs are low molecular weight compounds that stabilize the native conformation of a mutant enzyme in the endoplasmic reticulum. Usually competitive inhibitors of the enzyme, this stabilization occurs by their interaction with the active site of the enzyme, allowing the mutated enzymes to avoid premature degradation. The stabilized enzyme can then be transported to the lysosome where the large amount of built-up substrate is believed to displace the PC and take over the stabilization role (and be acted upon by the enzyme). Pyrimethamine has been shown to act as a PC for HexA; stabilizing the enzyme until it is displaced by glycolipid intermediates in the lysosome. Studies have shown pyrimethmine to enhance residual enzyme levels in late-onset gangliosidoses patients by up to four times (Maegawa et al. 2007) for certain mutations.

Thus, gene therapy with co-administration of a pharmacological agent as described herein may provide a synergistic approach to GM2 gangliosidoses treatment.

Embodiments will be further described by way of the following non-limiting Example.

EXAMPLE

Animal Cohorts

Animal cohorts are outlined in Table 1. Controls consisted of mice heterozygous (Het) for mutations to the HexB gene (−/−) and (+/−), and vehicle injected KO mice. Treatment groups consisted of SD mice injected with therapeutic AAV vector carrying the genes of interest alone, or combined with pyrimethamine, indomethacin, or ITF2357.

TABLE 1

Animal cohorts

| Genotype | Treatment | Number in Cohort |
| --- | --- | --- |
| Heterozygote (+/−) | None | 6 |
| Sandhoff mouse (−/−) | PBS Injection (postnatal day 1) | 6 |
| Sandhoff mouse (−/−) | HexBP2AHexA Injection (postnatal day 1) | 3 |
| Sandhoff mouse (−/−) | Indomethacin (daily) | 6 |
| Sandhoff mouse (−/−) | Pyrimethamine (daily) | 6 |
| Sandhoff mouse (−/−) | ITF2357 (daily) | 6 |

Experimental Animals

The hexb−/− experimental mice were obtained from Jackson Laboratories. From these, a colony was established at Queen's University through heterozygous breeding (hexb+/−). Genotyping of the mice was carried out via PCR amplification from animal ear punches taken at the time of weaning (three weeks of age). Experimental animals were obtained through mutant cross breeding (hexb−/−). The mice were maintained on a 12-hour light cycle from 7 am to 7 pm. All experimental protocols and procedures were performed in accordance with and were approved by the Queen's University Animal Care Committee.

Viral Construct

Figure 1B:
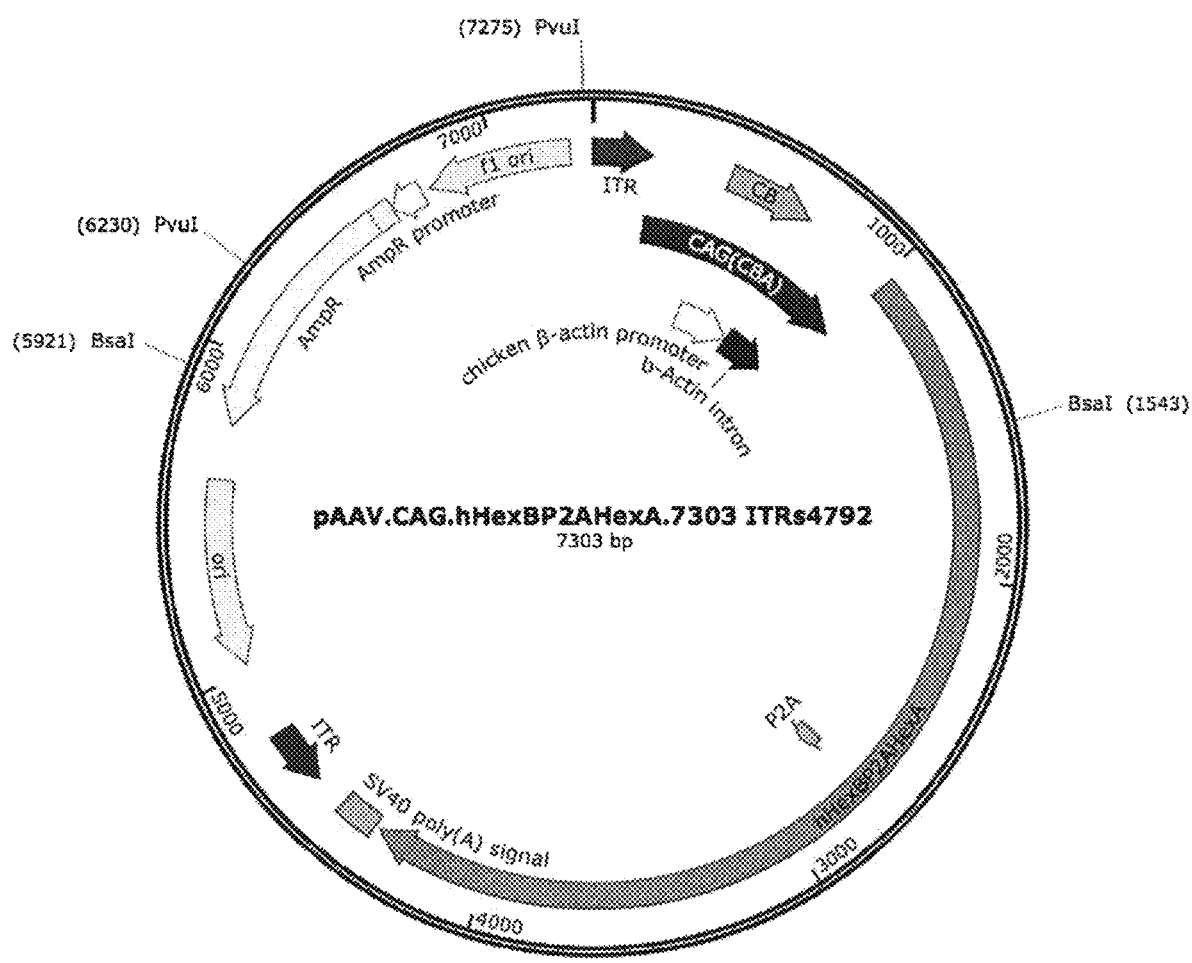
FIG. 1B is a diagram showing an AAV9 HEXB-HEXA vector construct, according to one embodiment.

The HEXB-HEXA ssAAV9 plasmid sequence included cDNA of the human HEXB gene (NCBI Reference Sequence: NM_000521) and the human HEXA gene (NCBI Reference Sequence: NM_000520) linked by a 2A self-cleaving peptide derived from porcine teschovirus (P2A). This construct was under the control of the CAG promoter, a ubiquitous synthetic promoter for high levels of gene expression in mammalian cells (Jun-ichi et al. 1989; Hitoshi et al. 1991). BioBasics (Markham, Ontario) synthesized the construct into a plasmid. Viral vectors were produced as previously described (Gray et al. 2013) and packaged into AAV9 serotype at a size of 4209 bp, well under the maximal limitations of the vector. Diagrams of the vector construct are shown in FIGS. 1A and 1B. The complete nucleic acid sequence is shown in SEQ ID NO:1 (FIG. 1C). A table showing the nucleotide numbering for various parts of the construct is shown in FIG. 1D.

Vector Delivery

Neonatal mice were intravenously injected with the ssAAV/HEXB-HEXA vector or a vehicle injection through the superficial temporal vein on day 0-1. Each treated mouse received an injection of $2.04 \times 10^{10}$ vg/mouse in a volume of 50 uL PBS with 350 nM NaCl and 5% sorbitol (vehicle). Untreated mice received an injection of 50 uL vehicle. During the injections, the dames were removed from the pups and placed in a clean cage. The cage of the pups alone was placed on a heating pad to keep them warm. Pups were then removed from the cage, one at a time, and placed over an LED light to aid in visualization of the superficial temporal vein. The pups received the injection using a 30 gauge needle and 1 mL syringe. After the injection, pressure was applied to the mouse using sterile gauze and the pup was returned to the home cage. The dame was returned to the cage with the pups following the completion of all injections. Pups were then monitored closely for several days to ensure survival.

Drugs

Starting at eight weeks of age, each drug treatment cohort received pyrimethamine, indomethacin, or ITF2357 at a dose of 1 mg/kg/day. Drug treatments were administered in the morning of the 12-hour light cycle via oral gavage using a 22 g curved feeding needle from Kent Scientific. ITF2357 was dissolved in ddH2O by heating to 85° C. while stirring for 1 hour. Indomethacin and pyrimethamine were each dissolved in 0.5% methylcellulose by heating to 80° C. while stirring for 1 hour. Each of these was stored at 4° C. for up to 2 weeks.

Live Animal Assessment

Behavioural testing was carried out on a bi-weekly basis from the age of eight weeks until each end point. The behavioural testing was done in three different parts and always assessed in the morning of the 12 hour light cycle.

Inverted Screen Test: Used to assess muscle strength of the mouse. In this test, the mouse was placed in the center of a wire mesh screen which was then rotated to an inverted position over the course of 2 seconds with the mouse's head declining first. Held 20 cm above a padded surface, the time elapsed before the mouse falls off was noted or the test was stopped when a maximum of 60 seconds was reached. Each mouse was given three trails spaced five minutes apart and the best trial was recorded for comparison.

Open Field Test: Used to assess overall locomotion and activity levels. The mouse was placed in a 40 cm×40 cm arena with walls. Time moving, rearing activity and the distance travelled were all electronically recorded by an ActiMot system. Speed was calculated by dividing the distance travelled by the time moving. Each mouse underwent one five minute trial.

Righting Reflex: Used to assess mobility and deterioration of living quality. The mouse was placed in the supine position and the time elapsed until all four paws were on the surface was recorded. Righting reflex was carried out three times on each mouse, and the longest time to right itself was recorded. A maximum score of 10 seconds was used and indicated a humane end point had been reached.

Tissue and Serum Collection

Animal tissues were collected at designated 16 week end points and long term humane end points. The humane end points were determined by either <15% loss of peak body weight or an inability to right itself in 10 seconds. Euthanization was carried out via $CO_2$ asphyxiation followed by cardiac puncture and perfusion with 10 mL of chilled PBS. For biochemical analysis sections of the forebrain, midbrain, hindbrain, cervical spinal cord, and lumbar spinal cord were collected along with the heart, lungs, liver, spleen, kidney, gonads, and a section skeletal muscle. These were all frozen immediately for further processing. For histological purposes, sections of the midbrain and liver were collected, fixed in 4% paraformaldehyde overnight and then immersed in 100% ethanol until sent to the Queen's University Histology department for paraffin embedding. Additional midbrain sections were collected from a number of mice and frozen in liquid nitrogen. Blood was collected via the saphenous vein on a monthly basis starting at 8 weeks and continuing until the humane end point. Additionally, blood was collected via the cardiac puncture during euthanization. Serum was separated from blood samples by centrifugation of 4000 rpm for 10 min and frozen immediately for storage.

Measuring β-Hexosaminidase Activity

Total hexosaminidase activity and Hex activity was measured as previously described (Maegawa et al. 2007; Tropak et al. 2004). Briefly, samples of hexosaminidase enzymes were obtained from 400 μL of sonicated midbrain homogenates and the collected serum samples. Total hexosaminidase activity was determined through the use of the 4-methylumbelliferyl-2-acetamido-2-deoxy-β-D-glucopyranoside (4-MUG) assay, whereas the HexA enzyme activity alone was determined through the use of the 4-methylumbelliferyl-7-6-sulfo-2-acetamido-2-deoxy-β-D-glucopyranoside (4-MUGS) assay. Beta galactosidase activity was determined through the use of 4-methylumbelliferyl-β-D-galactopyranoside assay. In all assays, the enzyme breaks down the substrate to release a fluorescent signal. Both absolute and relative levels of the signal release were used to assess enzyme activity levels. Additionally, results were compared to the 4-methylumbelliferone (4-MU) standard curve. The midbrain samples were diluted to 1:10 in 1×PBS to complete the MUGS assays. Briefly, the samples were incubated with the fluorogenic substrate at 37° C. for 1 hour, then read on the plate reader with excitation wavelength of 365 nm and an emission wavelength of 450 nm.

GM2 Ganglioside Levels

Ganglioside extraction and visualization was performed as previously described (Folch et al. 1951; Tropak et al. 2010; Wherrett et al. 1963). Briefly, frozen midbrain sections were sonicated in 3×10-second bursts, spun down at 4°

C. on maximum speed for 20 minutes after which 300 μL of the supernatant was mixed with the pellet before beginning the extraction. Gangliosides were extracted by a series of dilutions and evaporations of the midbrain samples in methanol and chloroform solvents. These mixed ganglioside samples were then separated on a thin layer chromatography plate using a 55:45:10 chloroform:methanol:0.2% calcium chloride mobile phase. Bands were visualized using orcinol and plates were dried at 120° C. for 10 minutes. Densitometry analysis was performed comparing the intensity of the GM2 to the total ganglioside bands using ImageJ software. A mix of manufactured gangliosides is run as the standard control for each TLC plate.

Cell Culture

Hek293 cells with HEXB and HEXA knockout (ABKO) were obtained from Dr. Don Mahuran at the University of Toronto. These cells have been shown to express no hexosaminidase A activity, or activity of any other hexosaminidase isoenzyme. Cellular transfections were carried out using a standard calcium phosphate transfection protocol. ABKO cells were grown in two sets of 10 cm plates along with a 10 cm plate of wild type Hek293 cells. Following transfection of one plate of ABKO cells and WT 293 cells, cell lysates from each plate were obtained for DEAE protocol.

DEAE Protocol

Cell lysates were analyzed by ion-exchange chromatography on DEAE-cellulose (Martino et al. 1995). The chromatography was performed by using 1 mL column equilibrated with a wash buffer (25 mM NaCl in 10 mM NaPi pH 6.0). Proteins retained by the column were eluted using the wash buffer (fractions 2-16), elution buffer 1 (200 mM NaCl in 10 mM NaPi pH 6.0) in fractions 17-24 and elution buffer 2 (500 mM NaCl in 10 mM NaPi pH 6.0) in fractions 25-32. Fractions (200 uL) were collected and assayed for Hex activity with MUG substrate.

Abundant Activities of Hex Isozymes are Generated by Transient Transfection of Hek293 A/B KO Cell Lines ABKO cells express no HexA activity as assessed my MUG and MUGs assays. Following a calcium phosphate mediated transfection of ABKO cells with plasmid containing the HEXB-HEXA construct, cells expressed all three isoforms of the hexosaminidase enzyme HexB, HexA, and HexS. Of clinical relevance is the HexA enzyme in levels which were shown to be greater than wild type Hek293 cells. DEAE elutions are shown in FIG. 2.

Figure 2:
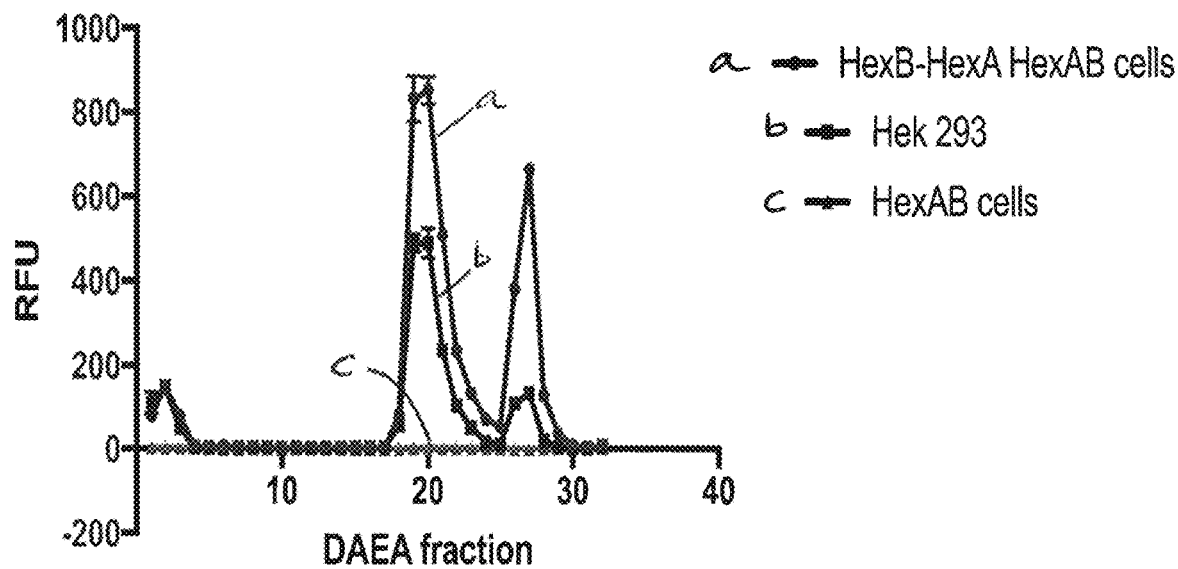
FIG. 2 is a plot showing activities of Hex isozymes generated by transient transfection of Hek293 A/B KO cell lines using a construct according to the embodiment of FIG. 1B.

FIG. 2 shows MUG assay DEAE fractions of cell lysates. Untransfected ABKO cells show no hexosaminidase activity. AAV9-HEXB-HEXA transfected ABKO cells and WT Hek293 cells both show hexosaminidase activity corresponding to each hexosaminidase isoenzyme. HexB (β/β) is represented by fractions 1-4, HexA (α/β) is represented in fractions 17-25, and Hex S (α/α) is represented in fractions 26-30. Transfected ABKO levels of hexosaminidase activity appear greater than the WT Hek293 in most elutions.

Impact of AAV-HEXB-HEXA on Survival and Motor Activity of SD Mice

To evaluate the efficacy of a single intravenous infection of rAAV9 expressing the human HEXA and HEXB cDNA in ameliorating the biochemical and neurological phenotype in SD, AAV9-HEXB-HEXA or a vehicle control was administered to postnatal day one neonates at a relatively low dose of $2\times10^{13}$ vg/kg via superficial temporal vein. Mice were all followed until they reached 32 weeks of age, or a humane end point.

Figure 3:
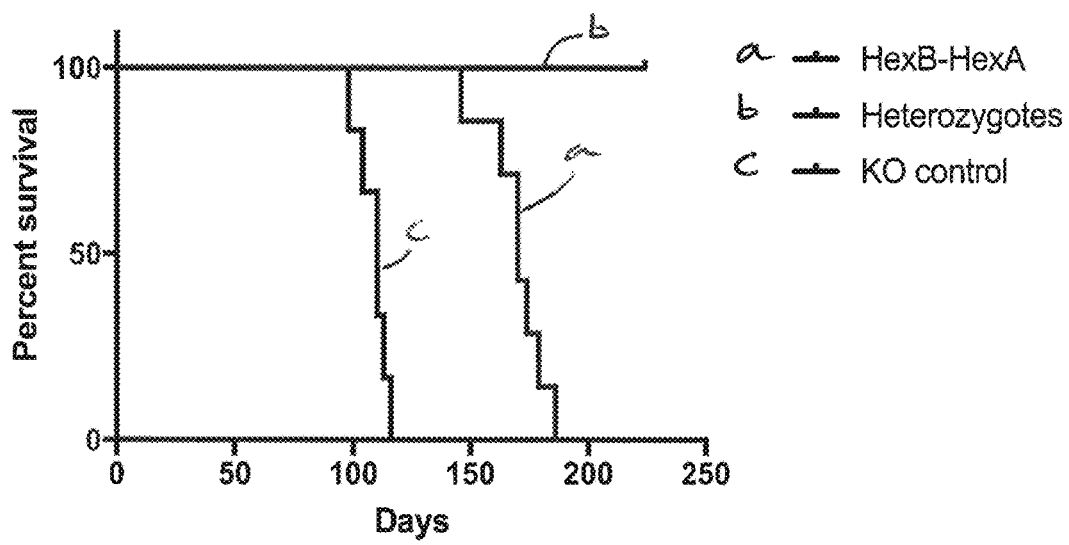
FIG. 3 is a plot showing impact of administration of a construct according to the embodiment of FIG. 1B on survival of mice.

Survival was analyzed with the log-rank (Mantel-Cox) test. Intravenous rAAV9 HEXB-HEXA gene delivery had a marked effect on lifespan compared to untreated SD mice (p=0.0002). This relationship is shown by the Kaplan-Meier plots in FIG. 3. Median survival for untreated SD mice was 110 days (n=6) and median survival for HEXB-11EXA treated mice was significantly greater at 170 days (n=6). 100% of heterozygous mice survived until the end of the study, as expected.

Figure 4:
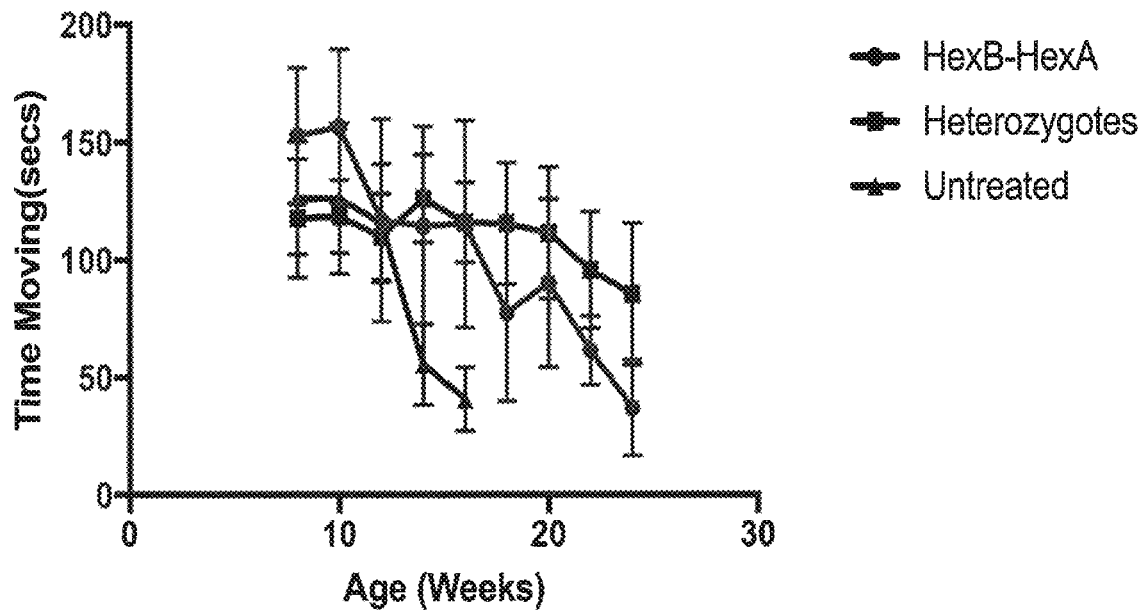
FIG. 4 is a plot showing effects of administration of a construct according to the embodiment of FIG. 1B on motor control in mice.

To determine if the administration of AAV9-HexB-HexA improved motor activity in the neonatally treated SD mice, distance travelled in the 5-minute open-field test was analyzed. Testing began at eight weeks, when motor deterioration in SD mice begins to show and continued on a bi-weekly basis to 24 weeks. No statistical difference exists until 16 weeks of age, when AAV9-HEXB-HEXA treated SD mice spent a significantly greater amount of time moving than the untreated controls (FIG. 4) indicating a lessening of their symptoms. In FIG. 4, values at each point represent the mean. Both heterozygous mice and HEXB-HEXA treated SD mice performed significantly better than untreated SD mice.

Effect of AAV-HEXB-HEXA Treatment of GM2 Ganglioside Storage

Figure 5:
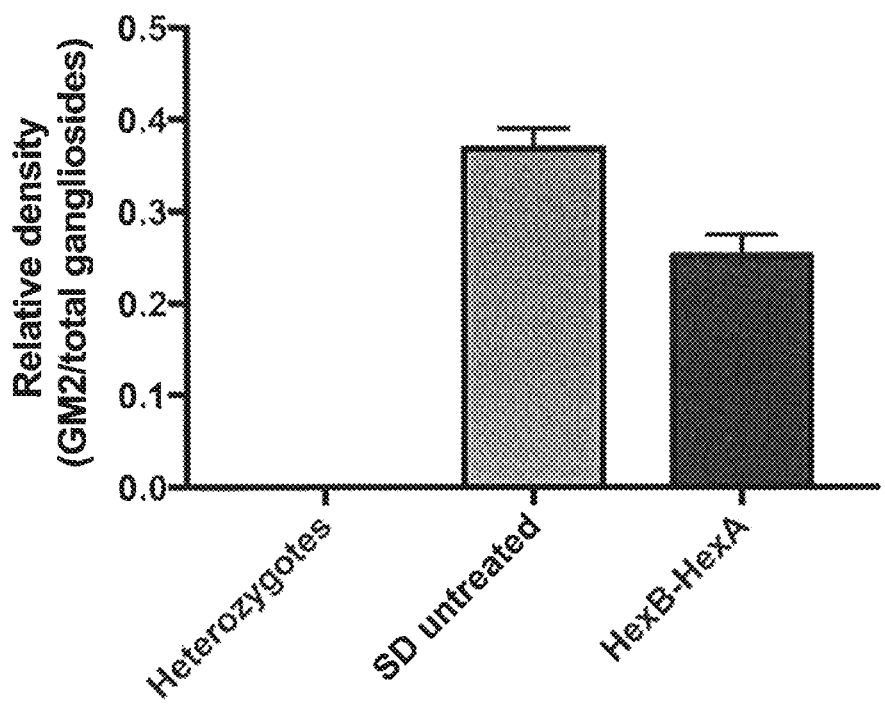
FIG. 5 is a plot showing effect of treatment with a construct according to the embodiment of FIG. 1B on GM2 ganglioside storage in mouse brain.

The increased survival and motor activity in SD mice treated neonatally with AAV9-HEXB-HEXA suggested that the intravenously-administered viral vector had crossed the BBB and transduced cells in the CNS. In doing so, the treatment was believed to have reduced the levels of GM2 ganglioside storage and increased HexA activity. To assess GM2 ganglioside in the brain high performance thin layer chromatography was used to examine ganglioside levels. GM2 ganglioside was not detectable in normal heterozygous mice but was found at relatively high levels in SD untreated mice. HEXB-HEXA treated SD mice showed significantly reduced levels of GM2 gangliosides in 16 week old mid brain sections (FIG. 5) compared to these untreated SD controls. Heterozygous mice showed no GM2 ganglioside build-up.

Figure 6:
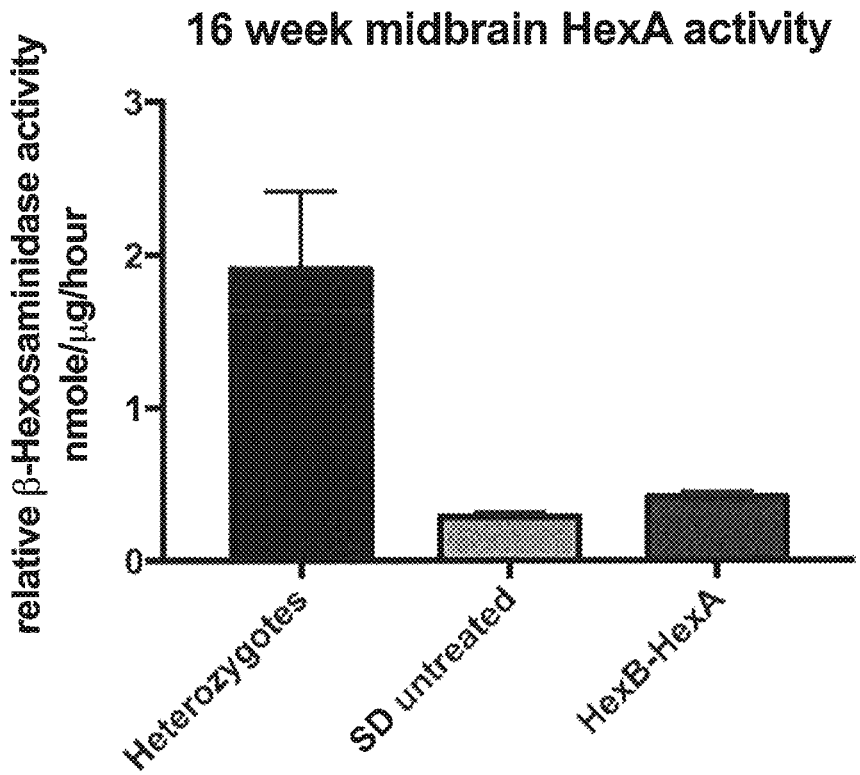
FIG. 6 is a plot showing effect of treatment with a construct according to the embodiment of FIG. 1B on HexA activity in mouse brain.

Consistent with the reduced GM2 ganglioside levels in the HEXB-HEXA treated SD mice; 16-week old midbrains of HEXB-HEXA treated mice showed a significantly higher level of activity compared to untreated SD mice. Both treated and untreated SD mice showed significantly lower levels of HexA activity then heterozygous mice (FIG. 6). In FIG. 6, columns represent relative brain HexA activity as a fraction of total beta galactosidase activity.

Effect of Drug Treatments on Survival and Motor Activity of SD Mice

Figure 7:
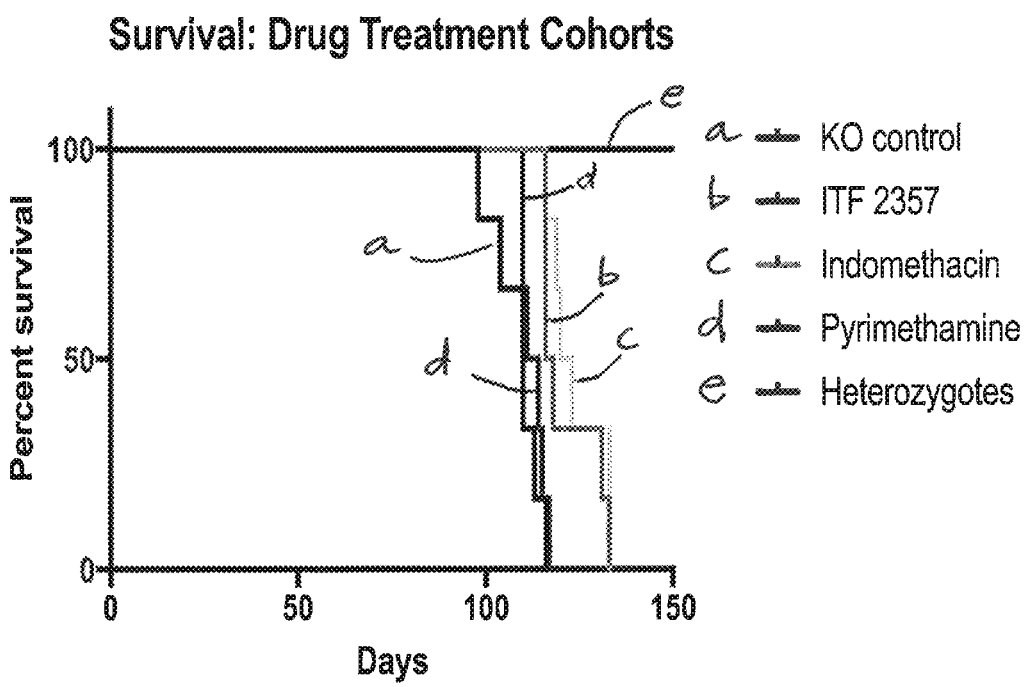
FIG. 7 is a plot showing effect of different anti-inflammatory drug treatments on survival and motor activity of SD mice.

Indomethacin, ITF2357, and pyrimethamine treated SD mice were assessed in comparison to untreated SD mice, as well as in combination with HEXB-HEXA therapy. Each drug was administered daily via oral gavage beginning at eight weeks of age. To assess the effectiveness of each treatment in ameliorating the symptoms and progression of the disease in the SD mice, survival analysis and behavior testing was undertaken. Both anti-inflammatory treatments indomethacin and ITF2357 were shown to have a significant effect on increasing survival time from 110 days in untreated SD mice (n=6) to 123.5 days in indomethacin treated mice (n=6) and 119 days in ITF2357 treated SD mice (n=6). Pyrimethamine did not have any significant effect on survival (mean=112.5 days, n=6). The survival results are shown by in the Kaplan-Meier plot of FIG. 7.

Additionally, motor activity was analyzed from week eight until week 16 through the open field test time moving parameter. Results showed no significant difference in amount of time moving for each week until week 16, when the untreated and pyrimethamine treated SD mice performed significantly worse than the heterozygous mice. No significant differences existed between the SD mice receiving anti-inflammatory treatments and heterozygous mice at 16 weeks.

Figure 8:
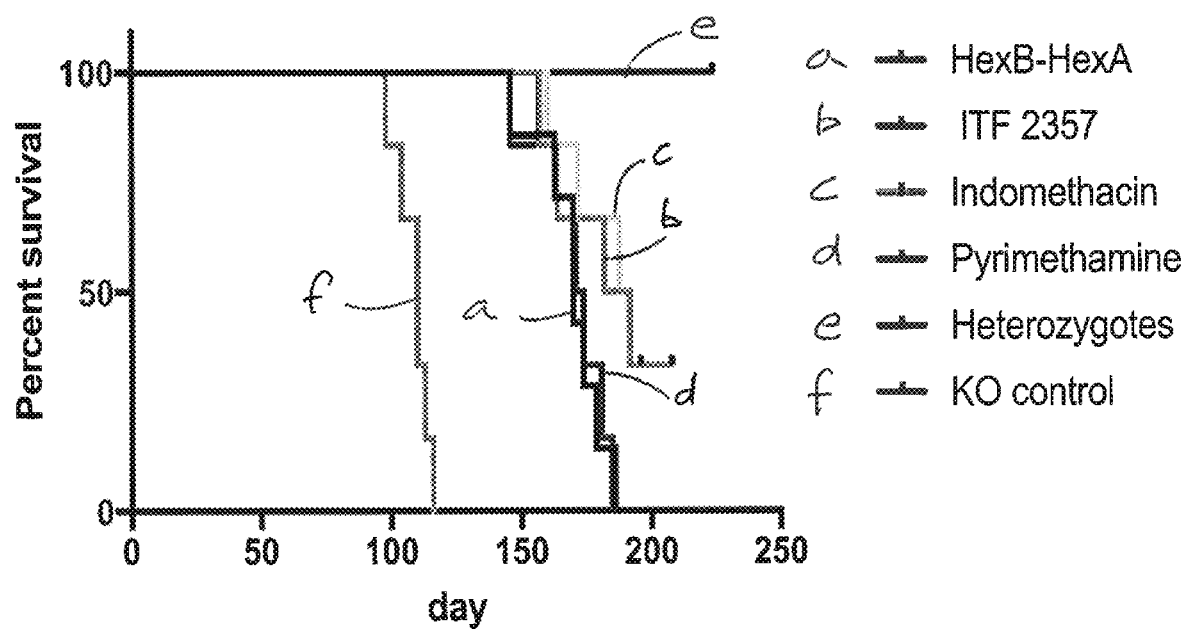
FIG. 8 is a plot showing effects of the combination of anti-inflammatory drug treatments with treatment with a construct according to the embodiment of FIG. 1B on survival of SD mice.

Indomethacin, ITF2357, and pyrimethamine were also assessed in conjunction with HEXB-HEXA neonatally treated SD mice. Again, AAV9-HEXB-HEXA was injected via the superficial temporal vein on neonatal day one at a dose of $2\times10^{13}$ vg/kg. These mice then began treatment with one drug at eight weeks of age via daily oral gavage. These treated mice were then followed until 32 weeks or their humane end point to assess the additive effects of gene and drug therapy. The combination of anti-inflammatory treatments with HEXB-HEXA had an additive effect as can be seen in the survival plot in FIG. 8. Indomethacin and ITF2357 treated SD mice showed a significant increase in survival and two mice in each group did not reach their humane end point after 210 days (n=6 for each). Pyrimethamine again had no statistically significant effect on SD mouse survival. Additionally, HEXB-HEXA treated mice that received either indomethacin or ITF 2357 showed a significant increase in mobility in the open field test at week 24.

Effect of Drug Treatments on GM2 Ganglioside Storage and HexA Activity

The mechanism that explains the observed increase in motor activity and survival with added treatment of anti-inflammatories is presumed to be a decrease in CNS inflammation. In order to eliminate a role of these drugs in HexA activity or GM2 ganglioside build-up, biochemical analysis of 16-week midbrain samples was again undertaken. No additional decrease in GM2 ganglioside build-up occurred with the treatment of indomethacin, ITF2357, or pyrimethamine, either on their own or in addition to HEXB-HEXA. Additionally, there was no further increase or decrease in HexA activity with the treatment of Indomethacin, ITF2357, or pyrimethamine, alone or in conjunction with HEXB-HEXA treatment.

Discussion

These results are the first to demonstrate the therapeutic potential of the HEXB-HEXA vector with the P2A linker construct. The data show that the gene construct produced functional HexA enzyme from the encoded β and α subunit in the ABKO cell line. Along with this, functional HexB and HexS isoenzymes were also produced. This initial in vitro expression provides proof of concept for the P2A linker vector construct, proving that both the β and α subunits are formed in sufficient quantities in the ABKO cell line to produce levels of hexosaminidase activity equal to or greater than wild type Hek293 cells following transfection.

In the mouse model a single relatively low dose (as compared to what is currently being used in clinical trials) of $2\times10^{13}$ vg/kg resulted in a significant increase in survival and improvement in behavioral phenotypes. These improvements were further corroborated through biochemical analysis that showed significant decreases in GM2 ganglioside build up and increased HexA activity in the midbrain of 16 week old mice. Whereas previous studies have shown the benefits of gene therapy for GM2 gangliosidoses, showing decreases in GM2 gangliosides or increases in HexA activity, previous approaches have been limited by the size of the HEXA and HEXB genes, both being so large that there is not enough room in AAV vectors, for a bicistronic vector, and/or by the need for administration directly to the brain. One option is to use viruses with larger capacity or multiple viruses carrying each gene, however these are typically viewed as more dangerous in terms of oncogenesis and have a limited ability cross the BBB and transduce neurons and other cells of the CNS. The HEXB-HEXA with a P2A linker construct described herein solves these problems. By using a small P2A linker, the cDNA of both HEXB and HEXA are able to fit into the single stranded (ss) AAV9 vector along with a ubiquitous promoter construct.

In the construct expression is driven by the strong synthetic promoter—CAG, which provides high levels of expression in mammalian cells so that both HEXB and HEXA subunits are expressed in high levels in each transduced cell. Cross correction, or enzyme transfer between cells in the CNS is known to occur with lysosomal enzymes including HexA. This means that a small number of transduced cells could act therapeutically for the entire central nervous system. Another important concept is the 'critical enzyme threshold' hypothesis, which suggests that an elevation in the level of enzyme in an affected individual to 5-10% of the wild type level could result in correction of the disease to the point where the individual can live a normal life.

Together these facts suggest that the HEXB-HEXA construct may provide a logical treatment solution. By expressing both subunits, a small number of cells overexpressing the HexA enzyme may be able to cross correct the entire animal, without being limited by the endogenous gene.

Evidence for the important role of inflammation has been well characterized in GM2 gangliosidoses and other related lysosomal storage disorders. Here again the results show that anti-inflammatory treatments on their own are able to extend life and ameliorate the symptoms of neurodegeneration to a significant degree with both indomethacin and ITF2357 treatment. This further supports the model that GM2 ganglioside build up results in an initial insult to neurons and cells within the CNS that triggers a self-perpetuating cycle of inflammation that results in further damage. By lessening this response, the disease can be delayed but not cured. In addition, this was the first time such an approach was used in conjunction with gene therapy. The results provide evidence of an additive effect of anti-inflammatory treatment with gene therapy. This provides a possible clinical treatment course that may be used in individuals that receive gene therapy and show the potential for inflammatory damage.

Additionally, pyrimethamine is known to play an important role in the clinical treatment of GM2 gangliosidoses with certain mutations. Pyrimethamine is known to increase the activity of some mutated versions of the HexA enzyme through an interaction with the active site that may allow for correct folding and a functional enzyme. This interaction however represents an interesting dilemma for treatment of SD disease with gene therapy as it was first identified as a competitive inhibitor of the HexA enzyme.

In SD mice there is no mutated enzyme formed, so pyrimethamine has no mechanism to ameliorate the disease phenotype and this is what was observed. However, when combined with HEXB-HEXA gene therapy, there is enormous potential for treatment interactions. This pharmacological chaperone had the potential to competitively either inhibit the HexA or assist in enzyme folding and trafficking. In this study, there was ultimately no significant effect of pyrimethamine on the HEXB-HEXA treated mice, neither a positive nor negative treatment interaction. This indicates that it may be possible that these two treatments be used simultaneously without negative interactions in a clinical setting. If so, individuals currently benefiting from pharmacological chaperone treatment would not have to discontinue that treatment in order to enroll in a gene therapy study.

All cited publications are incorporated herein by reference in their entirety.

EQUIVALENTS

While the invention has been described with respect to illustrative embodiments thereof, it will be understood that various changes may be made to the embodiments without departing from the scope of the invention. Accordingly, the described embodiments are to be considered merely exemplary and the invention is not to be limited thereby.

REFERENCES

Bera, L. A. "Adeno-associated virus gene therapy for Tay-Sachs disease", Master's thesis, University of Minnesota, Minneapolis, Minn., 2008.

Bourdenx, M., et al. "Systemic Gene Delivery to the Central Nervous System Using Adeno-Associated Virus" *Frontiers in Molecular Neuroscience* 7 (Jun. 2, 2014).

Faraco, G., et al. "Histone Deacetylase (HDAC) Inhibitors Reduce the Glial Inflammatory Response in Vitro and in Vivo" *Neurobiology of Disease* 36, no. 2 (November 2009): 269-79.

Folch, J., et al. "Preparation of Lipid Extracts from Brain Tissue" *Journal of Biological Chemistry*, 191(2) (1951): 833-841.

Foust, K. D., et al. "Intravascular AAV9 Preferentially Targets Neonatal Neurons and Adult Astrocytes" *Nature Biotechnology* 27, no. 1 (January 2009): 59-65.

Gray, S. J., et al. "Global CNS Gene Delivery and Evasion of Anti-AAV-Neutralizing Antibodies by Intrathecal AAV Administration in Non-Human Primates" *Gene Therapy* 20, no. 4 (April 2013): 450-59.

Guidotti J. E., et al. "Adenoviral gene therapy of the Tay-Sachs disease in hexosaminidase A-deficient knock-out mice" *Human Molecular Genetics* 8(5):831-8, 1999.

Hitoshi, N., et al. "Efficient Selection for High-Expression Transfectants with a Novel Eukaryotic Vector" *Gene* 108, no. 2 (Dec. 15, 1991): 193-99.

Jun-ichi, M., et al. "Expression Vector System Based on the Chicken β-Actin Promoter Directs Efficient Production of Interleukin-5" *Gene* 79, no. 2 (Jul. 15, 1989): 269-77.

Kim, J. H., et al. "High Cleavage Efficiency of a 2A Peptide Derived from Porcine Teschovirus-1 in Human Cell Lines, Zebrafish and Mice" *PLoS ONE* 6, no. 4 (Apr. 29, 2011).

Maegawa, G. H. B., et al. "Pyrimethamine as a Potential Pharmacological Chaperone for Late-Onset Forms of GM2 Gangliosidosis" *The Journal of Biological Chemistry* 282, no. 12 (Mar. 23, 2007): 9150-61.

Martino, S., et al. "Beta-N-Acetylhexosaminidases A and S Have Similar Sub-Cellular Distributions in HL-60 Cells" *Biochimica Et Biophysica Acta* 1243, no. 3 (Apr. 13, 1995): 489-95.

Sandhoff, K., et al. "Gangliosides and Gangliosidoses: Principles of Molecular and Metabolic Pathogenesis" The *Journal of Neuroscience: The Official Journal of the Society for Neuroscience* 33, no. 25 (Jun. 19, 2013): 10195-208.

Tropak, M. B., et al. "Pharmacological enhancement of beta-hexosaminidase activity in fibroblasts from adult Tay-Sachs and Sandhoff Patients" *Journal of Biological Chemistry* 279(14) (2004): 13478-87.

Tropak, M B., et al. "A Sensitive Fluorescence-based Assay for Monitoring GM2 Ganglioside Hydrolysis in Live Patient Cells and their Lysates" *Glycobiology*, 20(3) (2010): 356-365.

Wherrett, J. R., et al. "Detection and resolution of gangliosides in lipid extracts by thin-layer chromatography" *Biochemical Journal*, 86(2) (1963): 378-382.

Wu, Z., et al. "Effect of genome size on AAV vector packaging" *Molecular Therapy* 18(1)(2010): 80-86.

The invention claimed is:

1. A method for enhancing β-hexosaminidase A (HexA) enzyme activity in a subject in need thereof, comprising:
administering to the subject a therapeutically effective amount of a composition comprising
an AAV9 vector produced by expressing a construct in a cell, wherein said construct comprises a nucleotide sequence encoding from a 5' end to a 3' end a first ITR, a CAG promoter, a human HEXB gene, a self-cleaving P2A linker of 57 nucleotides, a human HEXA gene, and a second ITR;
wherein the self-cleaving P2A linker of 57 nucleotides links the HEXB gene and the HEXA gene;
wherein the nucleotide sequence from the beginning of the first ITR through the end of the second ITR consists of nucleotides 1 to 4792 of SEQ ID NO: 1.

2. The method of claim 1, wherein the subject is predisposed to having, suspected of having, or diagnosed as having a lysosomal storage disorder characterized by a deficiency in HexA expression or activity.

3. The method of claim 2, wherein the HexA deficiency comprises a partial or complete loss of endogenous expression or function of α-subunit of HexA encoded by the HEXA gene, β-subunit of HexA encoded by the HEXB gene, or both.

4. The method of claim 2, wherein the HexA deficiency is Tay-Sach's disease or Sandhoff disease.

5. The method of claim 4, comprising treating, reducing the severity of, or delaying the onset of Tay-Sach's disease and/or Sandhoff disease.

6. The method of claim 1, comprising administering the composition to the subject systemically.

7. The method of claim 6, comprising administering the composition to the subject intravenously.

8. The method of claim 1, wherein the subject is human.

9. The method of claim 1, comprising administering the composition to the subject intrathecally.

10. The method of claim 1, comprising further administering a therapeutically effective amount of at least one anti-inflammatory agent, or at least one pharmaceutical chaperone agent, or a combination thereof.

11. The method of claim 10, wherein the at least one anti-inflammatory agent comprises at least one agent selected from the group consisting of indomethacin and ITF2357.

12. The method of claim 10, wherein the at least one pharmaceutical chaperone agent comprises pyrimethamine.

* * * * *